(12) United States Patent
Zhao et al.

(10) Patent No.: US 8,613,894 B2
(45) Date of Patent: Dec. 24, 2013

(54) NUTRIENT RECOVERY SYSTEMS AND METHODS

(75) Inventors: Quanbao Zhao, Pullman, WA (US); Stephen W. Dvorak, Chilton, WI (US); Shulin Chen, Pullman, WA (US); Craig Frear, Pullman, WA (US); Bryan J. VanLoo, Lynden, WA (US)

(73) Assignees: DVO, Inc., Chilton, WI (US); Washington State University, Pullman, WA (US); Andgar Corporation, Everett, WA (US)

( * ) Notice: Subject to any disclaimer, the term of this patent is extended or adjusted under 35 U.S.C. 154(b) by 0 days.

(21) Appl. No.: 13/157,907

(22) Filed: Jun. 10, 2011

(65) Prior Publication Data

US 2012/0118035 A1 May 17, 2012

Related U.S. Application Data

(60) Provisional application No. 61/354,156, filed on Jun. 11, 2010.

(51) Int. Cl.
*C05D 9/02* (2006.01)

(52) U.S. Cl.
USPC .................. 423/168; 423/545; 422/630

(58) Field of Classification Search
USPC ............. 423/545; 422/630; 210/603; 71/32
See application file for complete search history.

(56) References Cited

U.S. PATENT DOCUMENTS

| 4,503,154 | A | 3/1985 | Paton |
| 5,015,384 | A | 5/1991 | Burke |
| 5,316,682 | A | * | 5/1994 | Keyser et al. ............... 210/649 |
| 5,670,047 | A | 9/1997 | Burke |
| 6,368,849 | B1 | 4/2002 | Norddahl |
| 6,451,589 | B1 | 9/2002 | Dvorak |
| 6,500,340 | B1 | 12/2002 | Burke |
| 6,613,562 | B2 | 9/2003 | Dvorak |
| 6,866,779 | B1 | 3/2005 | Burke |
| 6,946,076 | B2 | 9/2005 | Mills |
| 7,014,768 | B2 | 3/2006 | Li et al. |
| 7,078,229 | B2 | 7/2006 | Dvorak |
| 7,153,427 | B2 | 12/2006 | Burke |
| 7,166,220 | B2 | 1/2007 | Tanaka et al. |
| 7,179,642 | B2 | 2/2007 | Dvorak |
| 7,371,328 | B1 | 5/2008 | Hokanson et al. |

(Continued)

FOREIGN PATENT DOCUMENTS

| CA | 1161577 | 1/1984 |
| DE | 4415017 | 11/1995 |

(Continued)

OTHER PUBLICATIONS

Equivalent-Abstracts: Inorganic Chemistry.

(Continued)

*Primary Examiner* — Colleen Dunn
*Assistant Examiner* — Haytham Soliman
(74) *Attorney, Agent, or Firm* — Whyte Hirschboeck Dudek S.C.

(57) ABSTRACT

Methods, systems, and apparatuses for anaerobic digestion of waste fibrous material and the recovery of nutrients are provided. Methods, systems, and apparatuses disclosed herein provide mechanisms to release dissolved gases from anaerobic digester effluent. Methods, systems and apparatuses disclosed herein can recover one or more nutrients from anaerobic digested effluent using a range of temperatures, aeration rates, aeration times, pH ranges, and settling times.

12 Claims, 19 Drawing Sheets

(56) References Cited

U.S. PATENT DOCUMENTS

| | | |
|---|---|---|
| 7,410,589 B2 | 8/2008 | Lakshman |
| 7,604,740 B2 | 10/2009 | Baur |
| 7,785,467 B2 | 8/2010 | Logan et al. |
| 7,806,957 B1 | 10/2010 | Burke |
| 7,811,455 B2 | 10/2010 | Burke |
| 7,909,995 B2 | 3/2011 | Jiang et al. |
| 8,202,721 B2 | 6/2012 | Dvorak |
| 2002/0096471 A1 | 7/2002 | Miller, III |
| 2003/0038078 A1* | 2/2003 | Stamper et al. ............ 210/603 |
| 2004/0164019 A1 | 8/2004 | Fassbender |
| 2004/0164021 A1 | 8/2004 | Li et al. |
| 2006/0278587 A1* | 12/2006 | Schien et al. ............ 210/769 |
| 2007/0101783 A1 | 5/2007 | Gross et al. |
| 2007/0102352 A1 | 5/2007 | Burke |
| 2008/0053909 A1 | 3/2008 | Fassbender |
| 2008/0156726 A1 | 7/2008 | Fassbender |
| 2009/0062581 A1 | 3/2009 | Appel et al. |
| 2009/0206028 A1* | 8/2009 | Jiang et al. ............ 210/603 |
| 2010/0032370 A1 | 2/2010 | Allen et al. |

FOREIGN PATENT DOCUMENTS

| | | |
|---|---|---|
| JP | 61133200 | 6/1986 |
| JP | 2002079299 | 3/2002 |
| KR | 100414917 | 12/2003 |
| WO | 2004011393 | 2/2004 |

OTHER PUBLICATIONS

Frear, C. et al, "An integrated Pathogen Control, Ammonia and Phosphorus Recovery System for Manure and/or Organic Wastes," Washington State University, Deaprtment of Biological Systems Engineering, May 11-12, 2011.

Jiang, A. et al. "Integrated ammonia recovery technology in conjunction with dairy anaerobic digestion," CFF Final Report—AD Componet, Jun. 4, 2010.

Frear, C. et al., "An integrated nutrient recovery, Class-A fiber production process, and h2S scrubbing system that works in series with dairy manure anaerobic digesters-farm-scale demonstration on two Washington State dairies with digesters." NRCS CIG WSU Nutrient Recovery.

Zhao, Q. et al., "Phosphorous recovery technology in conjunction with dairy anaerobic digestion." CFF Final Report—AD Component.

International Search Report and Written Opinion for PCT App. No. PCT/US2011/040061 mailed on Feb. 29, 2012.

International Preliminary Report on Patentability mailed on Dec. 14, 2012 for PCT App. No. PCT/US2011/040061.

Examination Report for New Zealand Pat. App. No. 604050 mailed on Jul. 29, 2013.

* cited by examiner

FIG. 9A
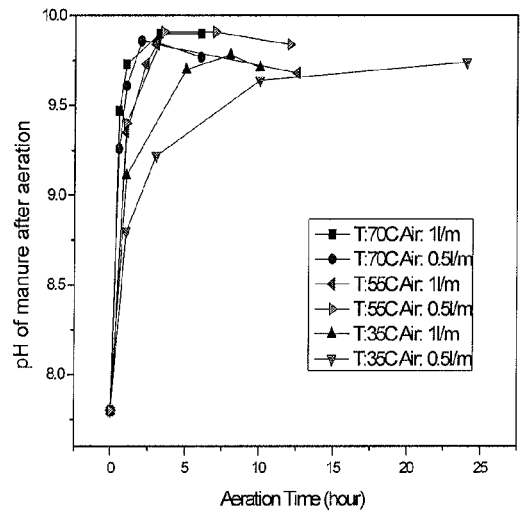
FIG. 9B
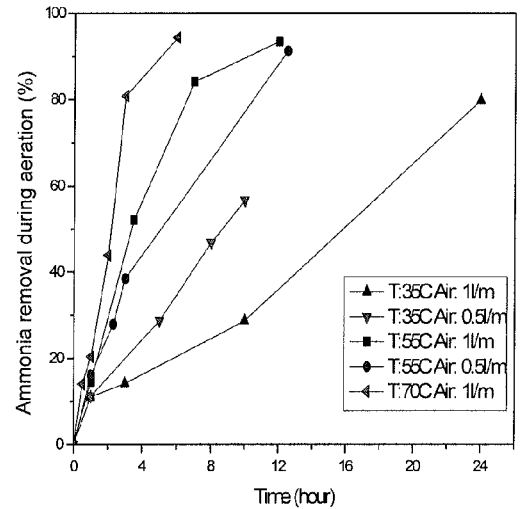
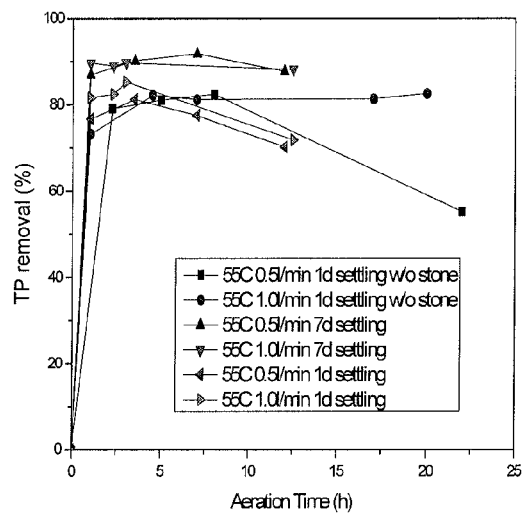
FIG. 9C

NUTRIENT RECOVERY SYSTEMS AND METHODS

CROSS REFERENCE TO RELATED APPLICATIONS

This application claims priority to U.S. Provisional Patent Application Ser. No. 61/354,156, filed Jun. 11, 2010, which is herein incorporated by reference in its entirety.

REFERENCE TO GOVERNMENT GRANT

This invention was made with United States government support awarded by the United States Department of Agriculture ("USDA"), Project Number 2008-5511218840; USDA SBIR Phase-I Award No. 2009-33610-19713, and USDA Project Contract No. 69-3A75-10-152. The United States has certain rights in this invention.

FIELD

Methods, systems and apparatuses disclosed herein relate to waste-processing systems for processing manure and recovering nutrients. Methods, systems and apparatuses disclosed herein relate to carbon and nutrient management tools.

BACKGROUND

Livestock confinement facilities generate large amounts of animal waste that can create serious environmental and human health concerns. For example, animal waste constituents such as organic matter, nitrogen, phosphorus, pathogens and metals can degrade water quality, air quality, and adversely impact human health. Organic matter, for example, contains a high amount of biodegradable organics and when discharged to surface waters will compete for, and deplete the limited amount of dissolved oxygen available, causing fish to die and other undesirable impacts. Similarly, nutrient loading from nitrogen and phosphorus can lead to eutrophication of surface waters.

The annual accumulation of organic waste in the world is immense. There are approximately 450,000 Animal Feeding Operations ("AFOs") in the United States. Common types of AFOs include dairies, cattle feedlots, and poultry farms. A single dairy cow produces approximately 120 pounds of wet manure per day. The waste produced per day by one dairy cow is equal to that of 20-40 people. If properly stored and used, manure from animal feeding operations can be a valuable resource.

Anaerobic digester technology is a manure management technology capable of alleviating environmental concerns through waste stabilization, odor reduction, pathogen control and greenhouse gas entrapment and mitigation, while producing a renewable source of heat and power (US-EPA, 2005). Adoption of anaerobic digesters on US dairies is growing but still slow with numbers insufficient to meet the agreement between the US and its dairy industry to reduce climate impacts from dairies by 25% by 2020 (USDA, 2010). An important concern in the adoption of anaerobic digester technology resides in the fact that anaerobic digester units do not recover nutrients. This is important because dairy Commercial Animal Feeding Operations (CAFOs) experience nitrogen and phosphorous overloads of 36% and 55%, respectively (USDA-APHIS, 2004).

Impacts of potential farm overloads express themselves in many air and water quality threats. High concentrations of ammonia can result in odors and can also interact with other air constituents to produce particulate matter ($PM_{2.5}$) (US-EPA, 2004), which is detrimental to human health. The U.S. agriculture industry is dependent on nitrogen-based fertilizers, which in turn is dependent on natural gas as the primary source of hydrogen to yield ammonia during the nitrogen-fixing Haber process. Clearly, technologies or mechanisms capable of collecting and concentrating existing, under-utilized forms of nitrogen, such as that present in manure waste streams, could play an important role in diminishing concerns that exist with inorganic fertilizer production.

Within water quality, leaching and excessive land applications are capable of transporting nitrogen and phosphorous compounds to the ground and surface water. Ionic ammonia and its inorganic derivatives, nitrite and nitrate, are harmful to both human and aquatic animals, with ammonia being toxic to fish, nitrite being a known carcinogen, and nitrate capable of causing blue baby syndrome and pregnant miscarriage (WS-DOH, 2005).

Phosphorous has long been implicated as a major contributor to water body eutrophication. Concerns regarding peak phosphorous levels potentially outweigh concerns associated with energy costs with nitrogen fertilizer. Numerous reports have shown that rock phosphate reserves could be exhausted during the next 50-100 years. In addition, sources will be tied to a few particular countries with quality of product diminishing, and cost of extraction increasing (Smil, 2000). With animal manures typically containing phosphorous:nitrogen ratios two to three times the normal ratio required for crop fertilization, it is easy to see why CAFOs struggle with phosphorous-loading to fields. However, concentrated sources of phosphorous and nitrogen, such as those available on CAFOs, could represent a viable source for recycled phosphorous, if economically viable technologies could be commercialized, which could potentially delay concerns regarding availability and demand.

These environmental threats can be, in part, diminished through incorporation of nutrient recovery technology capable of concentrating and exporting nutrients from the farm. Nutrient recovery also allows for wider adoption of bio-based fertilizers, replacing, at least in part, the demand for fossil-fuel based fertilizers and all of the climatic/environmental concerns associated with their production.

Several traditional wastewater technologies exist for the control and recovery of nutrients from human and industrial wastewater, however, these technologies are not cost effective or reliable when applied to manures within a farm environment. Thus, a need still exists for methods and apparatuses to recover nutrients from anaerobic digester waste material.

BRIEF SUMMARY

Methods, systems and apparatuses herein provide a unique and novel process that achieves high nutrient recovery rates with ease of operation and reduced operating and capital costs.

Methods, systems and apparatuses disclosed herein provide for a continuous, plug flow process for recovering nutrients from anaerobic digester effluent. Methods, systems and apparatuses disclosed herein can be used to increase the quantity of biogas capture from the anaerobic digester.

Methods, systems and apparatuses disclosed herein can be used to recover one or more nutrients from anaerobic digester effluent using a range of temperatures, aeration rates, aeration times, pH ranges, settling times, and the amount, if any, of quicklime or caustic, and size and shape of bubbles in the effluent.

Methods, systems and apparatuses disclosed herein have extensive flexibility and can be altered to achieve a desired outcome. The methods, systems and apparatuses can be modified to recover one specific nutrient or more than one nutrient.

In one embodiment, methods, systems and apparatuses disclosed herein can be used to produce fibrous, bio-fertilizer products and peat, as well as liquid effluent, which is considered a Class A effluent in regard to pathogen control, thereby significantly reducing concerns of zoonotic transfer between manure and crop fields.

In one embodiment, methods, systems and apparatuses disclosed herein can be designed to recover total phosphorous using aeration or aeration and temperature without focusing on pathogen control or ammonium salt recovery.

In another embodiment, methods, systems and apparatuses disclosed herein can be designed to recover total phosphorous, recover ammonia and control pathogens.

In an embodiment, methods, systems and apparatuses herein provide for the production of Class A biosolids and Class A effluent.

In one embodiment, a method for recovering a nutrient is disclosed comprising: heating and aerating anaerobic digester effluent in an aeration reactor to convert soluble ammonium to gaseous ammonia; providing gaseous ammonia from the aeration reactor to a stripping tower, said stripping tower providing controlled amounts of acid that reacts with gaseous ammonia; and recovering an ammonium salt produced from reacting the acid with gaseous ammonia in the stripping tower. In another embodiment, aerating the anaerobic digester effluent is accomplished using micro-aerators that aerate the effluent at a rate from 5 gallons/cfm to 25 gallons/cfm. In yet another embodiment, the method further comprises pumping the anaerobic digester effluent from the aeration reactor to a solids settling system prior to, after or simultaneously providing the gaseous $NH_3$ to the stripping tower. In still yet another embodiment, the method comprises collecting phosphorous-rich solids from the solids settling system.

In another embodiment, a method for recovering a nutrient is disclosed comprising: heating anaerobic digester effluent containing fibrous solids and suspended solids to about 160° F.; separating fibrous solids from the suspended solids in the effluent; heating and aerating the effluent in an aeration reactor to convert soluble ammonium to gaseous ammonia; providing gaseous ammonia from the aeration reactor to a stripping tower, said stripping tower providing controlled amounts of acid to react with gaseous ammonia; and recovering an ammonium salt produced from reacting the acid with $NH_3$ in the stripping tower. In another embodiment, the stripping tower is a two tank system.

In one embodiment, methods herein comprise aerating anaerobic digester effluent to remove dissolved gases including but not limited to carbon dioxide ($CO_2$), and methane ($CH_4$). Through aeration, the dissolved gases, such as $CO_2$ and methane, become supersaturated when exposed to air and can be released. $CO_2$ and methane become supersaturated because of the low partial pressure of $CO_2$ and methane in the air. Part of bicarbonate (HCO3-) can also be transferred to $CO_2$ and then be released to air by aeration. In another embodiment, the method comprises heating the effluent to a desired temperature and aerating to release dissolved gases and increasing the pH of the effluent.

In one embodiment, methods, systems and apparatuses herein provide for aerating anaerobic digester effluent to remove dissolved gases including but not limited to carbon dioxide ($CO_2$) and methane ($CH_4$). Through aeration, the dissolved gases, such as $CO_2$ and methane, become supersaturated when exposed to air and can be released. In another embodiment, the systems and apparatuses herein provide for heating the anaerobic digester effluent to a desired temperature. In one embodiment, engine exhaust or other waste heat from the anaerobic digester can be used to increase the temperature of the effluent.

In one embodiment, methods, systems and apparatuses disclosed herein comprise altering the ionic charge around suspended phosphorous colloids, and lowering the energy barrier to coagulation/settling.

In one embodiment, methods, systems and apparatuses disclosed herein comprise lowering the pH value of a liquid effluent that remains after recovering nutrients to a pH value suitable for use or application to a farm or field. In one embodiment, gas scrubbing can be used to lower the pH of the liquid effluent. In another embodiment, biogas comprising hydrogen sulfide ($H_2S$) is used with gas scrubbing to lower the pH value of the liquid effluent and reduce the amount of the $H_2S$ in the return biogas piped into the digester. Not to be bound by any particular theory, the $H_2S$ in the biogas reacts with the effluent, thereby decreasing the pH of the effluent and reducing the amount of $H_2S$ in the biogas.

In an embodiment, a method for recovering a nutrient is provided comprising: heating and aerating anaerobic digester effluent in an aeration reactor; providing gaseous $NH_3$ to a stripping tower, wherein controlled amounts of acid contact the $NH_3$; and recovering an ammonium salt. In yet another embodiment, the method comprises pumping the anaerobic digester effluent from the aeration reactor to a settling weir. In yet another embodiment, the method comprises using dewatering weirs to collect phosphorous-rich solids. In another embodiment, the method comprises bubbling biogas through the effluent from the settling weir.

In a further embodiment, a method for recovery of a nutrient is provided comprising: heating and aerating anaerobic digester effluent, which releases dissolved gases from the effluent and increases the pH of the effluent. Upon aeration, the dissolved gases become supersaturated. In an embodiment, heating anaerobic digester effluent comprises using a heat exchanger with the exhaust from a biogas engine gen set as the heated air stream.

In yet a further embodiment, a method for recovery of nutrients is provided comprising: digesting waste fibrous material in an anaerobic digester; separating digested fibrous material from effluent; aerating anaerobic digester effluent; heating anaerobic digester effluent to a temperature from about 140° F. to about 170° F.; pumping the anaerobic digester effluent to a solids/liquid separator; settling the separated liquid effluent; increasing the pH value of the separated liquid effluent to a value ranging from 9.0 to 11.5; settling the liquid effluent for a second time; and recovering one or more than one nutrient rich solid. In one embodiment, the pH value is increased by aerating and heating the effluent.

In an embodiment, a method for recovery of a nutrient is provided comprising: digesting waste fibrous material in an anaerobic digester; separating digested fibrous material from effluent; heating the effluent in an effluent pit; aerating and heating anaerobic digester effluent to a temperature from about 140° F. to about 170° F.; increasing the pH value of the liquid effluent to a value ranging from 9.0 to 11.5; settling the liquid effluent; and recovering one or more than one nutrient rich solid.

In another embodiment, the method further comprises capturing ammonium salt by passing $NH_3$ through a stripping tower that releases controlled amounts of acid. In yet another embodiment, the method further comprises passing the liquid effluent after nutrient recovery through a heat exchanger. In still another embodiment, the method further comprises heating waste material in the anaerobic digester with the heat from the heat exchanger. In still yet another embodiment, the method comprises passing the liquid effluent from the heat exchanger to a gas scrubbing system with biogas comprising $H_2S$. In one embodiment, the concentration of $H_2S$ in the biogas is reduced to a value ranging from 25 parts per million (ppm) to 115 ppm or from 50 ppm to 100 ppm or from 60 ppm to 90 ppm.

In still another embodiment, a nutrient recovery system is provided comprising: an aeration reactor for aerating and heating anaerobic digester effluent; and an acid tower for mixing acid with $NH_3$ from the aeration reactor. In another embodiment, the aeration reactor comprises micro-aerators at or near the floor of the reactor for injection of gas. In yet another embodiment, the nutrient recovery system further comprises an anaerobic digester for digesting waste fibrous material. In yet another embodiment, the nutrient recovery system comprises an effluent pit for heating anaerobic digester effluent. In still another embodiment, the nutrient recovery system further comprises a solids settling system for collection of the effluent from the aeration reactor. In another embodiment, the nutrient recovery system further comprises a separator for separating fibrous solids from the effluent prior to heating the effluent in the effluent pit.

In still another embodiment, a nutrient recovery system is disclosed comprising: an aeration reactor for heating and aerating anaerobic digester effluent, wherein heating and aerating the effluent converts soluble ammonium to gaseous ammonia; a stripping tower for mixing controlled amounts of acid with gaseous ammonia from the aeration reactor; and a vessel for collecting an ammonium salt produced from reacting acid with gaseous ammonia in the stripping tower. In yet another embodiment, the stripping tower is a two tank system.

In yet another embodiment, a nutrient recovery system is provided comprising: an anaerobic digester; an effluent pit for heating and aerating anaerobic digester effluent; a solid/liquids separator; and an air-tight vessel. In one embodiment, the system provides for a continuous plug-flow process. In another embodiment, the system further comprises one or more gas stripping towers, and one or more than one heat exchangers.

In one embodiment, the air-tight vessel comprises three chambers with a head space for collection of gas. In yet another embodiment, the air tight vessel comprises two chambers with a head space for collection of gas.

In an embodiment, an apparatus for the recovery of nutrients is provided. In one embodiment, the apparatus comprises a three-chambered vessel with a gas headspace above the liquid level and below the vessel ceiling. In an embodiment, the three-chambered vessel will be air-tight and operated under a vacuum.

In one embodiment, the apparatus comprises a two-chambered vessel with a gas headspace above the liquid level and below the vessel ceiling. In an embodiment, the two-chambered vessel will be air-tight and operated under a vacuum.

An advantage of the methods, systems and apparatuses disclosed herein is nutrient recovery from anaerobic digester effluent.

An advantage of the methods, systems and apparatuses disclosed herein is the recovery of nutrients while minimizing chemical addition and the use of energy resources.

An advantage of the methods, systems and apparatuses disclosed herein is the recovery of significant levels of nitrogen and phosphorous from anaerobic digester effluent.

An advantage of the methods, systems and apparatuses disclosed herein is that the separated solids and phosphorous rich solids will be organic.

An advantage of the methods, systems and apparatuses disclosed herein is a system that can be tailored and optimized to recover a specific nutrient or nutrients.

An advantage of the methods, systems and apparatuses disclosed herein is the optimization of operating parameters to account for various manure types with minimal energy and inputs.

An advantage of the methods, systems and apparatuses disclosed herein is that animal waste solids do not have to be removed prior to anaerobic digestion or prior to operations of the nutrient recovery system.

BRIEF DESCRIPTION OF THE DRAWINGS

FIG. 9A is a line graph reporting the effect of aeration and temperature on pH.

FIG. 9B is a line graph reporting the effect of aeration and temperature on $NH_3$ removal.

FIG. 9C is a line graph reporting the effect of aeration and temperature on total phosphate removal.

Figure 1:
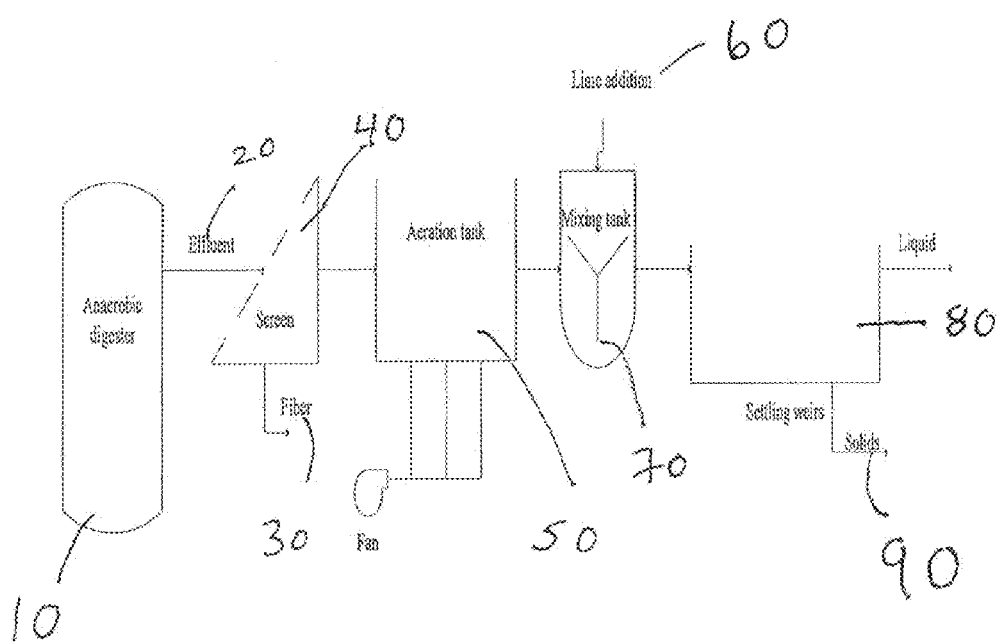
FIG. 1 is a schematic overview of one embodiment of a nutrient recovery process.

Before one embodiment is explained in detail, it is to be understood that the methods, systems and apparatuses disclosed herein are not limited in application to the details of construction and the arrangements of the components set forth in the following description or illustrated in the drawings. The methods and apparatuses are capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the singular forms "a," "an," and "the" refer to one or more than one, unless the context clearly dictates otherwise.

As used herein, the term "aeration reactor" refers to a chamber, vessel, apparatus or enclosure that allows for introduction of gas, air, liquid or a combination thereof into an effluent. The effluent can contain solid components.

The term "Class A biosolid(s)" and "Class A effluent" and "Class A liquid" as used herein refers to material that has met the requirements of 40 C.F.R. §503.32. In general, EPA Class A pathogen requirements are met in biosolids when fecal coliform densities are less than 1,000 Most Probable Number (MPN) per gram total solids (dry weight density); or when Salmonella densities are less than 3 MPN per four grams total solids at the time the sewage sludge is used or disposed; at the time the sewage sludge is prepared for sale or give away in a bag or other container for application to the land; or at the time the sewage sludge or material derived from sewage sludge is prepared to meet the requirements of the various alternatives under §503.32. Enteric virus density must be less than one plaque-forming unit (pfu) per four grams of total solids (dry weight basis) and helminth ova is less than one viable helminth ova per four grams of total solids. Additionally, the EPA provides time and temperature requirements under 40 CFR §503.32(a) 40 C.F.R. §503.32 is herein incorporated by reference as the standard for Class A biosolids.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

As used herein, "gas super saturation" occurs when the partial pressure of one or more gases becomes greater than that of the atmosphere.

As used herein, the term "manure" refers to animal wastes including animal dejections, feed remains and hair.

As used herein, the term "quicklime" is calcium oxide (CaO). Quicklime is a white, caustic and alkaline crystalline solid at room temperature. As a commercial product, lime often also contains magnesium oxide, silicon oxide and smaller amounts of aluminum oxide and iron oxide.

As used herein, the term "struvite" (ammonium magnesium phosphate) is a phosphate mineral with formula: $((NH_4)MgPO_4 \cdot 6H_2O)$. Struvite crystallizes in the orthorhombic system as white to yellowish or brownish-white pyramidal crystals or in platey mica-like forms. It is a soft mineral with Mohs (the Mohs scale of mineral hardness) of 1.5 to 2 and has a low specific gravity of 1.7. It is sparingly soluble in neutral and alkaline conditions, but readily soluble in acid.

Methods, systems and apparatuses disclosed herein can be used to recover nutrients from anaerobic digester effluent. In one embodiment, methods, systems and apparatuses disclosed herein are aimed at the recovery of phosphorous, the recovery of nitrogen, or the recovery of phosphorous and nitrogen.

In one embodiment, methods, systems and apparatuses disclosed herein provide for the release of dissolved gas from anaerobic digester effluent. In another embodiment, methods, systems and apparatuses disclosed herein provide for the release of dissolved gas from anaerobic digester effluent while maintaining the level of existing solids, such as calcium or magnesium bound to phosphates. Through aeration, the dissolved gases, such as $CO_2$ and methane, become supersaturated when exposed to air and can be released.

Methods, systems and apparatuses disclosed herein provide for a sterilized anaerobic digester effluent. Methods, systems and apparatuses disclosed herein provide for an anaerobic digester effluent and biosolids that fulfill the requirements to be classified as a Class A liquid or Class A solid.

In one embodiment, the methods, systems and apparatuses herein provide for integration, wherein the by-products from one unit of operation are used for treatment in a subsequent unit of operation. The major chemical and energy inputs to the system are waste heat, parasitic electrical loads, air, sulfuric acid, and raw biogas from the anaerobic digester. In exchange, multiple saleable nutrient products are developed—fibrous solids, ammonia sulfate slurry (ranging from 30% mass content to 55%), and phosphorous rich organic solids. Each product can be sold and used separately or two or more products can be mixed together for use or sale.

In one embodiment, a system is designed to work in conjunction with an anaerobic digester for the treatment and recovery of saleable concentrated bio-fertilizers from the anaerobic digestion effluent. Methods, systems, and apparatuses disclosed herein can work on any type of farm including a flush dairy farm and a scrape dairy farm.

In one embodiment, methods, systems and apparatuses disclosed herein comprise aeration technology to aerate the effluent from digested waste fibrous material to remove dissolved gases such as $CO_2$, and to increase the pH of the effluent. The pH of the effluent can be increased to a value ranging from 8.6 to 10.5. The increase in pH will aid in the settling of the solids. In another embodiment, methods, systems and apparatuses disclosed herein comprise the addition of an agent with a high pH value including but not limited to a caustic or quicklime to increase the pH to a value ranging from 8.6 to 12.0.

In one embodiment, systems disclosed herein have multiple levels of treatment possibilities. A system can be tailored to recover a specific nutrient or nutrients. For instance, for some farms, phosphorous control is the primary interest, and the system can be tailored to meet budget and environmental constraints. For example, aeration at reduced flow rates and temperatures but for longer periods of time will allow total phosphorous removal but no Class A biosolids or recovery of ammonia. On the other hand, aeration for less time with high temperature will achieve a pH that allows for total phosphorous removal and Class A biosolids but without much ammonia release. In addition, fiber can optionally be recovered depending on the end-users needs.

In an embodiment, methods, systems and apparatuses disclosed herein provide flexibility to recover a nutrient or nutrient of choice. One could achieve total phosphorous removal with longer aeration, and low temperature. Alternatively one could achieve total phosphorous removal with Class A fiber with shorter aeration with high temperature. On the other hand, one could achieve total phosphorous removal, ammonia removal and Class A with relatively longer aeration, high temperatures, increased aeration, and increased flow rate. Numerous possibilities exist by altering and adjusting various parameters of the system.

Methods, systems and apparatuses disclosed herein avoid the input and use of expensive chemical additives. The methods and apparatuses can be used to recover one or more than one element including but not limited to the recovery of total phosphorous, primarily in the form of previously suspended solids, ammonia salts, which were previously in the form of ionic ammonia within the manure, total nitrogen through recovery of the aforementioned ammonia as well as organic forms of nitrogen in the entrapped solids, and fibrous solids. Calcium and magnesium are also reduced in collecting the P solids.

Methods, systems and apparatuses disclosed herein can be used to reduce total phosphorous in the liquid effluent including but not limited to a reduction of 10-20%, 20-30%, 30-40%, 40-50%, 50-60%, 60-70%, 70-80%, 80-90%, 90-95%, and 95-99%.

Methods, systems and apparatuses disclosed herein can reduce total nitrogen in the liquid effluent from 15% to 85% or from 20% to 70% or from 30% to 50%.

Methods, systems and apparatuses disclosed herein can reduce bicarbonates in the liquid effluent from 5% to 15% or from 15% to 85% or from 20% to 70% or from 30% to 50%.

Methods, systems, and apparatuses disclosed herein can recover nutrients from the effluent including but not limited to a recovery of 5-10%, 10-20%, 20-30%, 30-40%, 40-50%, 50-60%, 60-70%, 70-80%, 80-90%, 90-95%, and 95-99% of the total nutrient. In an embodiment, the recovered nutrients include but are not limited to phosphorous, total nitrogen, and ammonia-N.

Methods for Nutrient Recovery

In an embodiment, methods for recovering nutrients from anaerobic digested effluent are disclosed. Use of the method need not be confined to agricultural endeavors or to the treatment of animal waste. For example, the methods may also be adapted and utilized by zoos, animal parks, or other organizations that care for multiple animals, or by municipalities to process human waste, etc.

In one embodiment, the methods comprise aerating liquid effluent to achieve a desired pH value. In another embodiment, the methods comprise heating anaerobic digested effluent to a desired temperature and aerating the effluent to achieve a desired pH value. In an embodiment, the desired pH value is a value that allows supersaturated gases to be released.

In yet another embodiment, the methods comprise heating anaerobic digested effluent to a desired temperature, aerating the effluent to achieve a desired pH value; and allowing solids in the aerated effluent to settle. In one embodiment, an agent with a high pH value is added during aeration, near the end of aeration, after aeration or before settling the liquid effluent. In an embodiment, the agent includes but is not limited to a caustic or quicklime, lye or lime.

In still yet another embodiment, the method further comprises mixing an agent with a high pH value to the effluent after settling. In another embodiment, the method further comprises passing the lime/effluent mixture to a second settling tank. In still another embodiment, the method further comprises collecting nutrient rich solids.

In another embodiment, methods for recovering nutrients from anaerobic digested effluent comprise anaerobically digesting waste fibrous material, separating activated sludge from liquid effluent; heating the anaerobic digester effluent to a desired temperature, aerating the liquid effluent to a desired pH value; passing the effluent through a separator; transporting the liquid effluent to a solids settling system, and recovering nutrient rich solids. In yet another embodiment, the method comprises mixing lime to the effluent after settling. In still another embodiment, the method comprises settling the lime/effluent mixture prior to recovering nutrient rich solids.

In another embodiment, a method for recovering nutrients is disclosed comprising aerating effluent to a pH value from 7.5 to 10.5 or from 8.2 to 9.5 or from 8.6 to 9.0. The method further comprises passing the aerated effluent through a solid/liquid separator; settling the aerated effluent for a period of time from 30 min. to 72 hours; adding an agent with a high pH value to achieve a pH value ranging from 8.6 to 12.0, settling the effluent/agent mixture for a period of time from 30 min to 72 hours. In another embodiment, the method comprises collecting the nutrient rich solids. In one embodiment, the solids are phosphorous rich.

In another embodiment, a method for recovering nutrients is disclosed comprising heating anaerobic digester effluent to a desired temperature; aerating the effluent to a desired pH value; plug flowing the effluent through a separation system; transporting the effluent to a settling tank for a period of time; mixing an agent with a high pH value with the effluent; settling the agent/effluent mixture for a period of time, and separating solids from liquid. In another embodiment, the method further comprises collecting nutrient rich solids.

The effluent can be heated to any desired temperature including but not limited to 100° F. to 110° F., 110° F. to 120° F., 120° F. to 130° F., 130° F. to 140° F., 140° F. to 150° F., 150° F. to 160° F., 160° F. to 165° F., 165° F. to 175° F., or 175° F. to 195° F.

In an embodiment, the aeration rate can be any rate that assists in the release of supersaturated gases including but not limited to from 2 gallons/cfm to 160 gallons/cfm, or from 5 gallons/cfm to 150 gallons/cfm, or from 10 gallons/cfm to 100 gallons/cfm or from 25 gallons/cfm to 80 gallons/cfm or from 40 gallons/cfm to 50 gallons/cfm. In an embodiment, micro-aeration socks can be used.

In an embodiment, the aeration time can be any amount of time that assists in the release of supersaturated gases including but not limited to from 15 min to 3 days, or from 2 hours to 2 days, or from 4 hours to 24 hours, or from 8 hours to 18 hours, or from 12 hours to 16 hours.

In an embodiment, aeration can increase the pH value of the effluent to a desired value including but not limited to 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0 and greater than 12.0.

In an embodiment, the aerated effluent is allowed to settle for a period of time including but not limited to 30 min to 60 min, 1 hour to 2 hours, 2 hours to 4 hours, 4 hours to 8 hours, 8 hours to 12 hours, 12 hours to 16 hours, 16 hours to 20 hours, 20 hours to 24 hours, 24 hours to 36 hours, 36 hours to 48 hours, 48 hours to 60 hours, 60 hours to 72 hours, 3 days to 4 days, 4 days to 5 days, 5 days to 6 days, 6 days to 7 days, 7 days to 8 days, 8 days to 9 days, 9 days to 10 days and greater than 10 days.

In an embodiment, the effluent is allowed to settle for a period of time including but not limited to 30 min to 60 min, 1 hour to 2 hours, 2 hours to 4 hours, 4 hours to 8 hours, 8 hours to 12 hours, 12 hours to 16 hours, 16 hours to 20 hours, 20 hours to 24 hours, 24 hours to 36 hours, 36 hours to 48 hours, 48 hours to 60 hours, 60 hours to 72 hours, 3 days to 4 days, 4 days to 5 days, 5 days to 6 days, 6 days to 7 days, 7 days to 8 days, 8 days to 9 days, 9 days to 10 days and greater than 10 days.

In an embodiment, nutrient rich solids include but are not limited to phosphorous rich solids, struvite-like particles, organic Ca/Mg bound phosphorous particles, and Class A biosolids.

FIG. 1 provides one embodiment of a method for nutrient recovery. The method comprises digesting waste fibrous material in an anaerobic digester 10. After a suitable period of digestion, separating the effluent 20 from the fiber 30 using a separation screen 40. Aerating the effluent 20 in an aeration tank 50, where air is injected into the liquid effluent. The aeration tank may comprise gas nozzles or jets at the bottom of the tank 50 to disperse air. The aeration can be in the form of micro-aeration.

An optional step involves mixing quicklime 60 with the effluent 20 in a mixing tank 70. The method further comprises transporting the lime/effluent mixture to a solids settling system 80, and collecting nutrient rich solids 90 including but not limited to phosphorous-rich solids.

Controlled aeration can be used to remove supersaturated $CO_2$, increase the pH value of the effluent, and enhance the settling of suspended solids. The aeration is purely chemical in nature. In one embodiment, a small and limited amount of aeration is used, just enough to control chemical equilibriums. The aeration used herein does not constitute an aerobic processing. The aeration will not result in the growth and proliferation of aerobic bacteria as is often observed in the biological treatment of wastewater. Wastewater treatment uses a vastly higher rate of aeration and for the sole purpose of aerobic bacteria growth.

Not to be bound by any particular theory, it is believed that the anaerobic digester effluent is very high in bicarbonates and dissolved $CO_2$ gases, due to the fact that during the anaerobic digester cycle, a significant portion of organic carbon has been converted to methane and $CO_2$, some of which in turn dissolves and/or supersaturates into solution. The dissolved $CO_2$ and part of bicarbonate (HCO3-) that is transferred to $CO_2$ hinders settling of suspended solids, interfering with the natural processes of gravity settling and/or charge-induced flocculation. The ionization formulas of carbonate carbonic acid, bicarbonate and carbonate are shown below in Equations 1-3.

$$CO_3^{2-}+H_2O \leftrightarrow HCO_3^-+OH^- \qquad (1)$$

$$HCO_3^-+H_2O \leftrightarrow H_2CO_3(l)+OH^- \qquad (2)$$

$$H_2CO_3 \leftrightarrow CO_2(g)+H_2O \qquad (3)$$

Not to be bound by any particular theory, it is believed that removing dissolved $CO_2$ and some of the bicarbonates, which is transferred to $CO_2$, from the anaerobic digester effluent will remove, at least a portion of the settling interference, and potentially allow for significant suspended solids settling without the need for artificial chemical inputs. Limited, controlled aeration of the anaerobic digester effluent can induce the removal of the dissolved $CO_2$ and some of the bicarbonates.

While aerating the effluent, $CO_2$ is taken out of the system by air. The equilibrium of reaction #3 moves right, as a result, equilibrium of reaction #2 and #1 move right. More $OH^-$ is then generated and the pH value of the solution is increased. Moreover, some crucial anaerobic bacteria will be killed by $O_2$ through aeration, which slows down on-going biological $CO_2$ generation.

During the aeration process of the effluent, the $CO_2$ is driven off and natural chemical equilibriums are shifted to also drive off some of the bicarbonates. Since dissolved $CO_2$ is an acidic compound, the pH of the solution rises, thus giving an indication to the extent to which the $CO_2$ has been removed. The pH of the effluent can also be used to determine if the appropriate level of aeration has been achieved and can be used as an indicator or marker for the amount of settling to expect.

As the pH increases, the $H_2CO_3$ portion in liquid decreases according to reaction #2. Therefore, the $CO_2$ stripping efficiency is decreased. This decrease in efficiency could result in the energy barrier not being completely overcome and the desired settling not occurring. In such a case, adding lime ($Ca(OH)_2$ or CaO) can become more efficient to increase pH than aeration and ultimately achieve the pH required to overcome the energy barrier to settling. Ionization formula of lime and reaction between lime and bicarbonate is depicted in Equations 4-6.

$$Ca(OH)_2 \leftrightarrow Ca^{2+}+2OH^- \qquad (4)$$

$$HCO_3^-+OH^- \rightarrow CO_3^{2-}+H_2O \qquad (5)$$

$$H_2CO_3+OH^- \rightarrow HCO_3^-+H_2O \qquad (6)$$

The aeration process of the anaerobic digested effluent will allow for enhanced suspended solids settling without the need for chemical inputs. Importantly, a majority of the phosphorous is in the form of tiny insoluble, suspended solids. During the anaerobic digestion process, much of the organic phosphorous is converted to an inorganic form, which is not available as phosphate or truly dissolved. Instead, high concentrations of calcium and magnesium ions in the manure have led to the production of insoluble, colloidal, non-crystalline solids that are suspended in solution as forms of calcium or magnesium phosphate. Thus, by enhancing suspended solids settling you directly result in the removal of significant amounts of phosphorous.

It is anticipated that some end-users of the methods, systems and apparatuses disclosed herein will only desire to recover phosphorous. In this case, careful control of aeration and pH can allow for recovery of phosphorous alone. To remove total phosphorous but not ammonia, the effluent can have a pH value ranging from 8.6 to 9.0. The temperature of the effluent is carefully controlled as well. For example, 20 hours of low aeration (40 gallons/cfm) using 20-35° C. effluent can achieve a pH of 9.0, which will provide good settling. Alternatively, 6 hours of aeration (40 gallon/cfm) using 35 C effluent can achieve a pH value of 8.6, which will also settle well.

However, other end users of the methods, systems and apparatuses disclosed herein may want to recover more than phosphorous. Increasing the pH of the anaerobic digester effluent can assist in shifting the chemical equilibrium from dissolved ammonia to gaseous ammonia and introduce a means by which ammonia and nitrogen can be removed and recovered from the anaerobic digester effluent. In an embodiment, anaerobic digested effluent with a pH value of 9.5 or greater and at a temperature of 140° F. or greater can provide for recovery of ammonia, likely in the form of liquid ammonium sulfate.

In another embodiment, controlled aeration rate/time (10-40 gallons/cfm for 1-7 hours) and temperature (55° C. to 70° C.) can achieve pH ranges between 9.5 and 10.0 allowing for significant ammonia volitization, stripping and recovery as an ammonia salt, preferably ammonia sulfate.

In one embodiment, the liquid effluent is allowed to settle for a suitable period of time to allow the solids to drop out of solution including but not limited to time periods in the range of 15 min to 7 days, or from 12 hours to 6 days, or from 24 hours to 5 days, or from 36 hours to 4 days, or from 2 days to 3 days.

In one embodiment, method for increasing the quantity of biogas capture from the anaerobic digester are provided comprising agitating the anaerobic digester effluent as it departs the anaerobic digester vessel. In another embodiment, the method further comprises placing the effluent in a thin film flow for faster liquid/biogas separation. In yet another embodiment, the method further comprises placing the anaerobic digester discharge process under a vacuum.

In one embodiment, the disclosure relates to a method for the recovery of nutrients from an anaerobic digester effluent comprising heating the anaerobic digester effluent (about 100° F.) from an existing commercial anaerobic digester unit to 160° F. using an extended engine exhaust heat recovery system. The effluent and its fibrous solids are heated in order to meet Class A pathogen standards. The Class A fibrous solids can be removed through mechanical screen separation using an inclined screen with screw press, The method further comprises aerating the remaining liquid with suspended solids in an aeration zone at operating temperatures of approximately 140° F. Aeration can occur in a dedicated plug-flow tank. The plug-flow tank can have any suitable retention time including but not limited to 1-5,5-10, 10-20, 20-25, 25-30, 30-50, 50-100, 100-200 or greater than 200 hour retention time. Aeration can be accomplished through the use of micro-aerators placed at the bottom of the tank to supply various degrees of aeration flow per gallon of treated effluent. Air was heated to temperature using engine exhaust heat sent through an air to air heat exchanger.

As described before, the aeration allowed for the stripping of super-saturated $CO_2$ gas. High temperature enhanced the kinetics, allowing for a more rapid release of the $CO_2$ and two important results. First the pH is increased and second, gases that interfere with natural flocculation and settling can be removed. The increase in pH (>9.5) allowed for a portion of the dissolved ammonia to shift its equilibrium towards free, gaseous ammonia.

The method further comprises transporting free, gaseous ammonia to a dedicated two-stage acid tower, where controlled amounts of acid contact the gaseous ammonia in the air and produce an ammonium salt. The two-tower approach was designed so that a neutral pH product with consistent maximum concentration (~40% by weight) could be achieved.

The method also comprises settling phosphorous-rich solids and collecting the solids using dewatering weirs.

The method further comprises bubbling raw biogas from the digester through the relatively hot effluent with elevated pH, and returning the effluent pH to neutral while also simultaneously in-part scrubbing the biogas of acidic $H_2S$ impurities. A final heat exchanger can be used to reclaim waste heat.

Nutrient Recovery System

Figure 2:
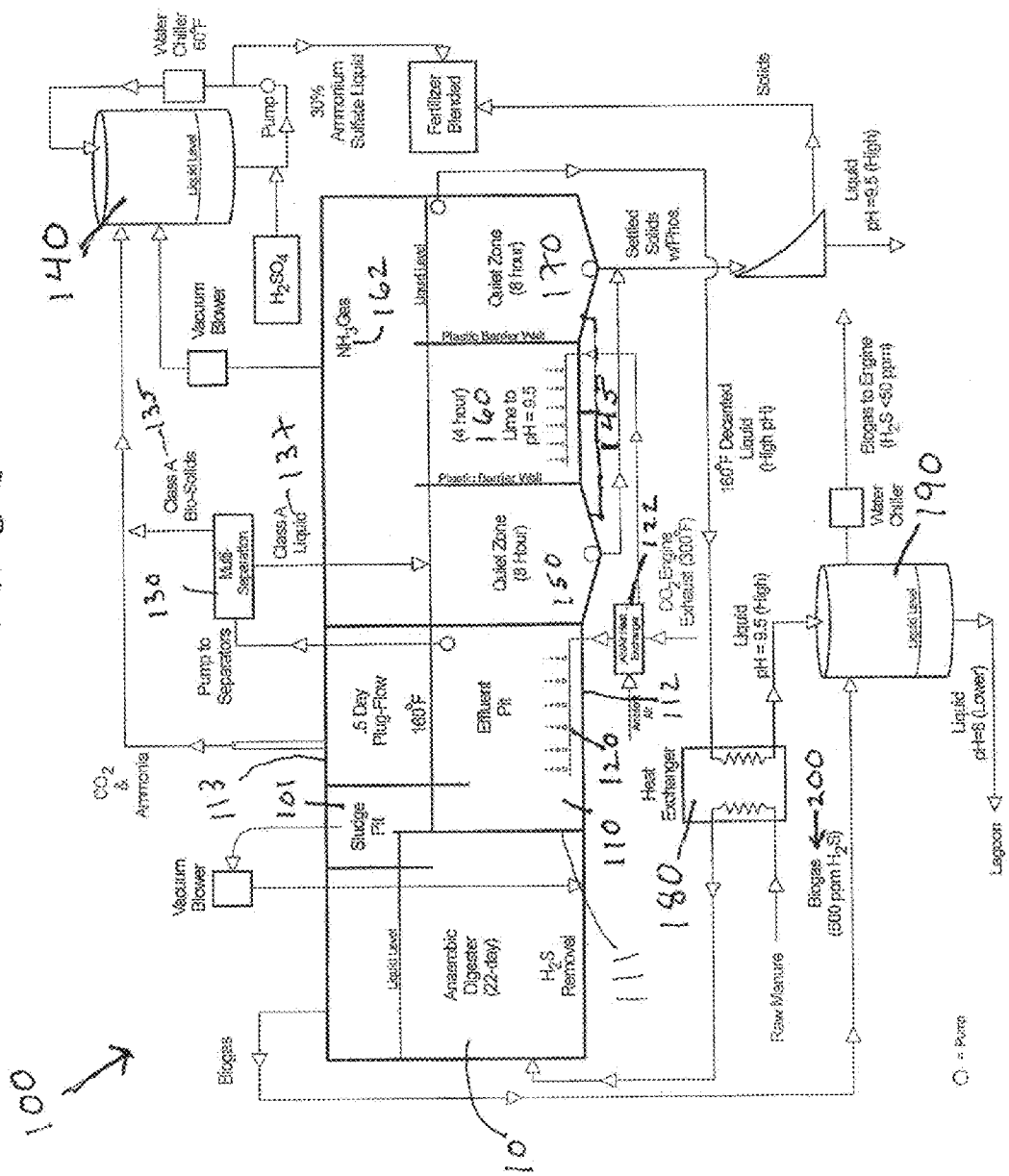
FIG. 2 is a schematic of one embodiment of a nutrient recovery system showing a three-chambered air-tight vessel.

In one embodiment, a nutrient recovery system 100 is illustrated in FIG. 2. The system 100 can be used to process anaerobic digester inputs and recover a nutrient from the resulting effluent. In one embodiment, the anaerobic digester input is waste fibrous material. Waste fibrous material may be collected using any suitable means in the art. Waste fibrous material includes but is not limited to wood, grass, agricultural residue, manure, recycled waste paper, organic fraction municipal solids, and agricultural waste materials. Examples of sources of waste fibrous materials include, but are not limited to, livestock production facilities, such as cattle, swine, goat, sheep, dairy cow, horse and the like, chicken ranches, turkey farms, duck farms, geese farms, human waste, and the like. Waste fibrous material may also include many forms of agricultural products processing facilities that may include non-food related agricultural products. Waste fibrous material may also include some forms of commingled wastes where a portion of the waste may also include food scraps. Waste fibrous material also may include commingled fibers with spoiled foods.

In another embodiment, the waste fibrous material also may include hay, straw, and other material commonly used in animal stalls or other agriculture environment. In yet another embodiment, the waste fibrous material also may contain urine plus water used in cleaning the stalls. In still yet another embodiment, the waste fibrous material may also contain additional material, such as twine, rope, and other material that may or may not be biodegradable. In yet another embodiment, the waste fibrous material is from a dairy farm.

In another embodiment, the waste fibrous material also may include fibers from non-food agricultural products such as bamboo, oil palm, coir, etc.

In another embodiment, the anaerobic digester input can comprise a mixture of animal manure and organic fraction municipal solids such as food scraps and food processing waste are co-mingled and digested.

FIG. 2 shows a schematic of the system 100 used to recover nutrients from processing high-solids farm waste. System 100 comprises inter alia an anaerobic digester 10, a sludge pit 101, an effluent pit 110, a separation device, 130, and an air-tight vessel 145.

Anaerobic Digester

Any type of anaerobic digester may be used. A conventional anaerobic digester system generally includes the following components: manure transfer and mixing pit, a digester made of steel, fiberglass, concrete, earth or other suitable material (including heating and mixing equipment if needed), biogas handling and transmission, and gas end use (combustion) equipment such as electric generation equipment.

Conventional anaerobic digesters can also require significant operational oversight depending on operational mode and temperature. Conventional anaerobic digester systems also require proper design and sizing to maintain critical bacterial populations responsible for waste treatment and stabilization for sustained long-term predictable performance. Sizing requirements are based on hydraulic retention time (HRT), and loading rate, where the operating temperature affects these sizing parameters. These factors (size, materials, operational requirements) affect digester costs, which may be fairly capital intensive, and in some economies and farm scales, may not be affordable or may be inoperable if experienced technicians are not available.

In one embodiment, anaerobic digesters having any type of process configuration can be used including but not limited to batch, continuous, mesophilic temperature, thermophilic temperature, high solids, low solids, single-stage complexity and multistage complexity.

In another embodiment, a batch system of anaerobic digestion can be used. Biomass is added to the reactor at the start of the process in a batch and is sealed for the duration of the process. Batch reactors suffer from odor issues that can be a severe problem when they are emptied. Typically biogas production will be formed with a normal distribution pattern over time. The operator can use this fact to determine when they believe the process of digestion of the organic matter has completed.

In yet another embodiment, a continuous system of anaerobic digestion can be used. In continuous digestion processes, organic matter is typically added to the reactor in stages. The end products are constantly or periodically removed, resulting in constant production of biogas. Examples of this form of anaerobic digestion include, continuous stirred-tank reactors (CSTRs), Upflow anaerobic sludge blanket (UASB), Expanded granular sludge bed (EGSB) and Internal circulation reactors (IC).

In still another embodiment, mesophilic or thermophilic operational temperature levels for anaerobic digesters can be used. Mesophilic temperature levels take place optimally around 37°-41° C. or at ambient temperatures between 20°-45° C.; under these temperatures, mesophiles are the primary microorganism present. Thermophilic temperature levels take place optimally around 50°-52° C. and at elevated temperatures up to 70° C.; under these temperatures, thermophiles are the primary microorganisms present.

There are a greater number of species of mesophiles than thermophiles. Mesophiles are also more tolerant to changes in environmental conditions than thermophiles. Mesophilic systems are therefore considered to be more stable than thermophilic digestion systems.

In another embodiment, anaerobic digesters can either be designed to operate in a high solid content, with a total suspended solids (TSS) concentration greater than 20%, or a low solids concentration with a TSS concentration less than 15%. High-solids digesters process a thick slurry that requires more energy input to move and process the feedstock. The thickness of the material may also lead to associated problems with abrasion. High-solids digesters will typically have a lower land requirement due to the lower volumes associated with the moisture.

Low-solids digesters can transport material through the system using standard pumps that require significantly lower energy input. Low-solids digesters require a larger amount of land than high-solids due to the increased volumes associated with the increased liquid: feedstock ratio of the digesters. There are benefits associated with operation in a liquid environment as it enables more thorough circulation of materials and contact between the bacteria and food. This enables the bacteria to more readily access the substances they are feeding off and increases the speed of gas yields.

In still another embodiment, digestion systems can be configured with different levels of complexity: one-stage or single-stage and two-stage or multi-stage. A single-stage digestion system is one in which all of the biological reactions occur within a single sealed reactor or holding tank. Utilizing a single-stage reactor reduces the cost of construction; however there is less control of the reactions occurring within the system. For instance, acidogenic bacteria, through the production of acids, reduce the pH of the tank, while methanogenic bacteria operate in a strictly defined pH range. Therefore, the biological reactions of the different species in a single-stage reactor can be in direct competition with each other. Another one-stage reaction system is an anaerobic lagoon. These lagoons are pond-like earthen basins used for the treatment and long-term storage of manures. In this case, the anaerobic reactions are contained within the natural anaerobic sludge contained in the pool.

In a two-stage or multi-stage digestion system, different digestion vessels are optimized to bring maximum control over the bacterial communities living within the digesters. Acidogenic bacteria produce organic acids and grow and reproduce faster than methanogenic bacteria. Methanogenic bacteria require stable pH and temperature in order to optimize their performance.

The residence time in a digester varies with the amount and type of waste fibrous material, the configuration of the digestion system and whether it is one-stage or two-stage. In the case of single-stage thermophilic digestion residence times may be in the region of 14 days, which comparatively to mesophilic digestion is relatively fast. The plug-flow nature of some of these systems will mean that the full degradation of the material may not have been realized in this timescale. In this event, digestate exiting the system will be darker in color and will typically have more odor.

In two-stage mesophilic digestion, residence time may vary between 15 and 40 days. In the case of mesophilic UASB digestion, hydraulic residence times can be (1 hour-1 day) and solid retention times can be up to 90 days. In this manner, the UASB system is able to separate solid and hydraulic retention times with the utilization of a sludge blanket.

Continuous digesters have mechanical or hydraulic devices, depending on the level of solids in the material, to mix the contents enabling the bacteria and the food to be in contact. They also allow excess material to be continuously extracted to maintain a reasonably constant volume within the digestion tanks.

In one embodiment, the waste fibrous material can be processed through an anaerobic digester available from GHD, Inc. (Chilton, Wis.). In one embodiment, the waste fibrous material can be processed through an anaerobic digester as described in any of U.S. Pat. Nos. 6,451,589; 6,613,562; 7,078,229; and 7,179,642; each of which are incorporated by reference in their entirety. Each of the patents recited above is assigned to GHD, Inc., and names Mr. Steve Dvorak as the sole inventor. In yet another embodiment, the anaerobic digester can be a two-stage mixed plug flow digester system In another aspect, the invention may provide a method for the anaerobic digestion of high-solids waste comprising moving the solid waste in a corkscrew-like fashion through the digester. The digester is a generally U-shaped tank with overall horizontal dimensions of approximately 100 feet long and 72 feet wide. A center wall approximately 90 feet in length divides the digester into the two legs of the U-shape. Thus, each leg of the digester is approximately 100 feet long and 36 feet wide.

Modified plug flow or slurry flow can be used to move the sludge. The digester heating pipes locally heat the sludge using hot water at approximately 160° F. from the cooler of the engine, causing the heated mixed sludge to rise under convective forces. The convection develops a current in the digester that is uncharacteristic of other high-solids digesters. Sludge is heated by the digester heating pipes near the digester center wall, such that convective forces cause the heated sludge to rise near the center wall. At the same time, sludge near the relatively cooler outer wall falls under convective forces. As a result, the convective forces cause the sludge to follow a circular flow path upward along the center wall and downward along the outer wall. At the same time, the sludge flows along the first and second legs of the digester, resulting in a combined corkscrew-like flow path for the sludge.

In another embodiment (not shown), hot gas injection jets using heated gases from the output of the engine replace the hot water digester heating pipes as a heating and current-generating source. The injection of hot gases circulates the sludge through both natural and forced convection. A similar corkscrew-like flow path is developed in the digester.

To further increase upward flow of the heated sludge near the center wall, biogas may be removed from the biogas storage area in the digester, pressurized with a gas centrifugal or rotary-lobe blower, and injected into the heated sludge through nozzles positioned onto conduit. This recycled biogas injection near the floor of the digester serves to increase the rapidity of the cork-screw-like flow path for the heated sludge.

The U-shape of the digester results in a long sludge flow path and thus a long residence time of approximately twenty days. As the sludge flows through the digester, anaerobic digestion processes the sludge into activated sludge. From the digester, the activated sludge flows into the optional clarifier and into a sludge pit 30. The clarifier uses gravity to separate the activated sludge into liquid and solid portions.

Effluent Pit

The nutrient recovery system comprises an effluent pit (20). The effluent pit is separated from the anaerobic digester (20) by a wall (111). The effluent pit and the anaerobic digester can share one or more common outer walls (112 and 113). The effluent pit can also comprise a head-space for collection of gas.

In one embodiment, the anaerobic digester effluent 20 can gravity flow, or it can be pumped, into an insulated effluent pit 110. In an embodiment, the anaerobic digester effluent is discharged from the digester, while maintaining gas integrity. The discharge of the anaerobic digester effluent is designed to maximize turbulence, thin film flow, and contact with outside air. This discharge process results in degassing of supersaturated methane gas for greater gas production and environmental/climate control.

In an embodiment, the resulting methane/air mixture can be re-injected into the anaerobic digester for enhancing mixing, and increasing biogas production. In addition, the re-injected methane/air mixture can aid in reducing hydrogen sulfide content in the digester.

The temperature of the anaerobic digester effluent 20 may be raised as it flows through the first vessel in a plug flow process to a suitable temperature including but not limited to 100° F. to 110° F., 110° F. to 120° F., 120° F. to 130° F., 130° F. to 140° F., 140° F. to 150° F., 150° F. to 160° F., 160° F. to 165° F., 165° F. to 175° F., and 175° F. to 195° F.

In an embodiment, the anaerobic digester effluent is heated using an extended exhaust heat recovery system to further heat treat the effluent and its fibrous solids to Class A pathogen standards.

The hydraulic retention time (HRT) of the effluent in the vessel can be verified according to U.S. EPA standards. HRT may vary, depending on design criteria, from 30 minutes to 48 hours or from 4 hours to 36 hours or from 8 hours to 24 hours or from 12 hours to 16 hours.

The effluent pit 110 will have a gas headspace above the liquid level and below the vessel ceiling, will be air tight, and will be operated under a vacuum. The effluent 20 in the effluent pit will be heated and agitated by the injection of heated gas, including but not limited to air, through injectors or gas nozzles 120. The heated gas will be injected into the liquid near the bottom of the effluent pit, causing a corkscrew mixing effect. Heated air can be supplied by taking ambient air through a cross-flow heat exchanger 122, with the exhaust from the bio-gas engine gen set providing the heated air stream. Heated effluent, agitated with air, will release the majority of the $CO_2$ and some of the $NH_3$ entrained in the liquid waste. Releasing the $CO_2$ from the liquid waste will cause a rise in pH in the liquid waste, increasing the $NH_3$ removal efficiency. The pH value can be used as a marker for how supersaturated gas has been released. The pH value also can be used as a marker to determine what nutrients can be recovered.

Not to be bound by any particular theory, it is believed that aeration allows for the generation of supersaturated gases, including but not limited to $CO_2$, and that high temperature enhances the kinetics, allowing for a more rapid release the supersaturated gases. By aerating the effluent, the pH value is increased and gases, which may interfere with natural flocculation and settling are removed.

In an embodiment, the aeration rate can be any rate that assists in the release of dissolved gases, which become super-saturated upon aeration, including but not limited to from 2 gallons/cfm to 160 gallons/cfm, or from 5 gallons/cfm to 150 gallons/cfm, or from 10 gallons/cfm to 100 gallons/cfm or from 25 gallons/cfm to 80 gallons/cfm or from 40 gallons/cfm to 50 gallons/cfm. In an embodiment, micro-aeration socks can be used.

In an embodiment, the aeration time can be any amount of time that assists the release of dissolved gases, which become supersaturated upon aeration, including but not limited to from 15 min to 3 days, or from 2 hours to 2 days, or from 4 hours to 24 hours, or from 8 hours to 18 hours, or from 12 hours to 16 hours.

In an embodiment, the aeration rate is selected to allow for stripping of dissolved gases, which become supersaturated upon aeration, and maintaining the level of existing solids such as calcium and magnesium bound phosphates. In an embodiment, the aeration rate does not cause dissolution of solids such as calcium and magnesium bound phosphates or struvite-like particles, which would release more free phosphates.

In an embodiment, aeration can increase the pH value of the effluent to a desired value including but not limited to 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0 and greater than 12.0.

In another embodiment, the aeration source is designed to produce bubbles of a particular size including but not limited to bubbles produced through microaeration.

Stripping Tower

The nutrient recovery system also comprises a stripping tower (140). The stripping tower is used for absorbing gaseous ammonia and stabilizing it to ammonium salt, solution, which can be more concentrated and easily stored. Briefly, stripping is a distillation procedure that consists of separating fluid components by differences in boiling point or vapor pressure. The usual means of separation is through a column or tower that is packed with one or more various support materials, i.e. Pall Rings, Raschig Rings, Berl Saddles, etc., to increase contact surface. A stripping medium (e.g. hot air or steam, or, in one embodiment, unheated air) is injected into the bottom of the tower and an ammonia containing solution is injected at or near the top. As the ammonia containing liquid trickles down through the packing, it contacts the rising hot vapor and the more volatile ammonia fraction is vaporized and can be collected and further treated. The less volatile liquid component becomes increasingly purer as it nears the bottom of the tower, where it may be collected. U.S. Pat. No. 7,909,995, which issued on Mar. 22, 2011, provides additional information on designs of stripping towers and nutrient recovery systems, and is expressly incorporated herein by reference in its entirety.

The stripping tower is an apparatus that can hold caustic acids including but not limited to sulfuric acid, nitric acid, carbonic acid, hydrochloric acid, and phosphate acid. The stripping towers can also comprise vacuum blowers and pumps.

In one embodiment, the stripping tower can be used to collect any ammonium salt including but not limited to ammonium carbonate, ammonium sulfate, ammonium chloride, ammonium nitrate, and ammonium phosphate.

As opposed to conventional methods that flow manure through stripping towers, plug flow aeration can be employed. This avoids clogging concerns that plaque stripping towers. In addition, conventional stripping towers focus on high efficiency through very high aeration rates. These aeration rates are often associated with pressure drops and high electricity demands.

In one embodiment, ammonia stripping is carried out using a closed loop tower design that uses air as the stripping medium and includes an acid absorption system to capture ammonia as ammonium salt. Air can be used for this process because, although it does not have as high an ammonia absorbance capacity as other potential carrier gases, air is inexpensive and the pH adjustment needed can be maintained at a relatively low level (e.g. pH 10) because the process takes advantage of the hot (about 32-35° C.) manure wastewater coming from the anaerobic digester to compensate.

In an embodiment, the effluent air, under vacuum in the effluent pit 110 will be transferred to a packed stripping tower 140 where a liquid wash of sulfuric acid, in this example, will drop the pH of the air stream and create a solution comprising ammonium sulfate. The solution can comprise an ammonium-salt slurry comprising from about 30% to about 60% ammonium sulfate. The ammonium sulfate can be collected and used as fertilizer.

In one embodiment, a single tower design may be used. A single tower includes waste water input for ammonia stripping and acid input for acid absorption. Air is directed into the bottom of the tower using the fan or blower. Air circulates in an enclosed system, thus allowing for enhanced ammonia recovery and a reduction in energy inputs as the air without outside influence maintains its temperature for a longer period of time. In some embodiments, the air is heated, e.g. to a temperature of about 50° C., or in the range of from about 40° C. to about 60° C.

Solid/Liquid Separator

The nutrient recovery system also comprises a solids/liquid separator (130) that can be used to separate liquids from solids. Any type of solid/liquid separator can be used. One example of a solids/liquid separator is the Puxin Manure Sludge Liquid Separator available from Shenzhen Puxin Science and Technology.

The Puxin separator is composed of a press machine, a sludge pump, a control cabinet and the pipelines. It is mainly used to separate the solid and liquid for livestock manure such as cow manure, pig manure and chicken manure etc. to get dry manure. The equipment works by continuous screw extrusion, and it can be applied to the manure or sludge with the size of solid particle ≥0.5-1.0 mm.

At the end of the engineered HRT, the entire sterilized anaerobic digester effluent will be pumped to a solids/liquid separator 130; resulting in a separated solids 135 stream that will meet Class A bio-solids criteria and a separator liquid stream 137 that will also be sterilized and pathogen free. The separated solids and separated liquid will be reduced in ammonia-N content. The ammonium sulfate created will be a higher-value utilization of the natural ammonium found in organic wastes and will be in a chemical form that is easier to utilize and market. The separated solids can be utilized for animal bedding, horticultural usage, or fertilizer.

Air-Tight Vessel Comprising an Aeration Reactor and Solids Settling System

The nutrient recovery system also comprises a single or multi-chamber air-tight vessel. The air-tight vessel can comprise one, two, three, four, five or more than five chambers. The chambers can share common walls or can be completely isolated. The chambers can have similar dimensions and designs, or unique dimensions or designs. Two or more than two chambers can have identical dimensions and designs. The chambers can be made of similar material or different material.

The separator liquid stream with a temperature maintained from 130° F. to 180° F. or from 140° F. to 160° F. can be transferred to a single chamber or multi-chamber air-tight vessel. A three chamber air-tight vessel 145 is shown in FIG. 2. The first chamber 150 is separated from the second chamber 160 by a barrier wall. The second chamber 160 is separated from the third chamber 170 by a barrier wall.

In an embodiment, the barrier wall can be made of any suitable material that keeps the chambers distinct including but not limited to plastic PVC, polyethylene, polypropylene, methacrylic or acrylic plastic, fiber glass reinforced plastic (FRP), or stainless steel.

In an embodiment, the first and third chambers can be in any shape or dimension that allows the desired outcome including but not limited to a rectangle, a square, a triangle, a circle, a pentagon and a V-notched shape. One or more pumps can be located at or near the floor of the first and/or third chambers.

a. The First Chamber

The first chamber 150, which may not be utilized in all configurations, will be a "quiet zone" chamber where the separator liquid will be allowed to decant. The large percentage of the minute solids that passed through the solids separator with the liquid effluent likely will settle to the bottom of the first chamber 150 and will be collected and removed for dewatering. Anaerobic digested liquids with decreased solids content, due to a separation proceess, and at a higher liquid temperature, separate faster and more efficiently. The liquid stream will plug flow through the first chamber 150, designed with an HRT from 30 minutes to 24 hours or from 60 minutes to 18 hours or from 2 hours to 16 hours or from 4 hours to 12 hours or from 8 hours to 10 hours. The liquid stream will plug flow into the second chamber 160.

b. The Second Chamber

The second chamber 160 can have any desired shape or dimensions that achieve the desired result including but not limited to a rectangle, a square, a circle, a triangle, a pentagon and a V-notched shape.

In the second chamber 160, the liquid stream may be gas-agitated with air that is heated in a heat exchanger with the $CO_2$ engine exhaust. Aeration allows for release of the supersaturated gases, which impeded settling. Nozzles or jets for injection of air into the second chamber can be located at or near the floor of the second chamber 160. In another embodiment, the liquid stream may be hydraulic-agitated with a recirculation pump, or can be mechanically agitated with a prop agitation system. In an embodiment, the agitation can be for a suitable period of time including but not limited to 30 minutes to 1 hour, 1 hour to 2 hours, 2 hours to 4 hours, 4 hours to 6 hours, 6 hours to 8 hours, 8 hours to 10 hours, 10 hours to 12 hours and greater than 12 hours. In this example, the second chamber serves as an aeration reactor.

In an embodiment, the liquid stream will have continuous agitation, which will aid in the removal of ammonia if removal is desired.

A high pH liquid including but not limited to quicklime or a caustic can be added to the separated liquid stream, upon entering the second chamber, to increase the pH of the liquid effluent to a suitable value including but not limited to 9.0-9.1, 9.1-9.2, 9.2-9.3, 9.3-9.4, 9.4-9.5, 9.5-9.6, 9.6-9.7, 9.7-9.8, 9.8-9.9, 9.9-10.0, 10.0-11.0, 11.0-12.0, 12.0-12.5, and greater than 12.5.

A benefit of decreasing the solids content of waste liquid is that less lime or caustic is needed to raise the pH of a given volume of liquid, thereby decreasing the chemical treatment cost of the nutrient recovery system. The liquid stream will plug flow through the second chamber 160 of the air-tight vessel 140 as it is agitated utilizing the mixed plug flow (corkscrew) agitation method described above in the section entitled Anaerobic Digeters, and will thereby maintain a consistent HRT in the vessel.

Increasing the pH of an anaerobic digester effluent to a pH about 9.5 or higher, at a temperature of 140° F. or greater, will convert soluble ammonium-nitrogen ($NH_4$—N) to non-soluble, volatile ammonia nitrogen ($NH_3$—N). The ammonia-nitrogen 162 will be volatilized rapidly with the continuous agitation provided in the air tight vessel and will be collected in the head space provided in the vessel. Vacuum extraction of the head space gases will be utilized to, further increase the volatilization rate inside the air tight vessel. Subsequently, by utilizing a system of air scrubbing the gaseous air stream with a low pH liquid solution of $H_2SO_4$ or similar acidic chemical, in a cross-flow air stripping tower 140, the ammonia will be removed from the air stream and captured as liquid ammonium sulfate. Ammonium sulfate is a highly valuable, easily solid fertilizer utilized by farmers and it will be an income stream for the nutrient removal system. Most importantly, the removal of the ammonium-nitrogen from the liquid waste stream solves one of the major disposal issues of the anaerobic digester effluent.

Importantly, in some applications, the end-user may desire not to recover nitrogen or ammonia. The system can be tailored to meet the needs and desires of the end-user. In an embodiment, a system can be designed to recover one or more than one component including but not limited to: (a) phosphorous; (b) recover ammonium salt for ammonia salt fertilizer; (c) Class A biosolids; (d) phosphorous and ammonium salt; (e) ammonium salt and Class A biosolids; (f) phosphorous and Class A biosolids; (g) phosphorus, ammonium salt and Class A biosolids. Controlling aeration rate, aeration time, and temperature of the effluent all aid in determining the nutrients recovered and the extent of the recovery.

c. Third Chamber

The liquid stream will plug flow into a third chamber 170, a "quiet zone" with no agitation where the liquid will be allowed to decant. The remaining solids will settle to the bottom of the third chamber, where they will be removed by a bottom discharge separation system. By the addition of quicklime, with its high pH and magnesium component, and the high temperature agitation that preceded the third chamber, a high level of magnesium-ammonium-phosphate easily and readily settles. The settled solids will be removed from the third chamber 160 and dewatered. In this example, the third chamber serves as a solids settling system.

In an embodiment, settling and dewatering of the nutrient rich solids is made easier through the use of a primary pump. In another embodiment, acid can be added to condense the solids layer for decanting.

Magnesium-ammonium-phosphate is also a highly valuable, easily sold fertilizer utilized by farmers and it will also be an income stream for the nutrient removal system. By removing the phosphorus and more ammonium from the liquid waste stream, the two largest disposal issues of the anaerobic digester effluent have been removed. The methods, systems and apparatuses disclosed herein contribute to solving many of the environmental and regulatory issues that generators/disposers of liquid organic wastes encounter in the US.

Heat Exchanger

The decanted liquid with a temperature from 140° F. to 175° F. will be pumped to a heat exchanger 180 where the temperature from the decanted liquid will be conserved by heating the cool incoming raw organic wastes at the front of the anaerobic digester system 10. This will conserve heat costs in the total system.

The decanted liquid will proceed from the heat exchanger 180 to a cross-flow, packed tower gas scrubbing system 190. In this gas scrubbing tower 190, the high pH decanted liquid will be exposed to the biogas 200 from the anaerobic digester system 10. The anaerobic digester biogas 200 typically has a hydrogen sulfate ($H_2S$) content of 500 ppm or higher and is considered very corrosive to the reciprocating engines utilized to convert the biogas into power for the electrical generation process.

The reaction in the stripping tower 190 of the high pH decanted liquids with the acidic $H_2S$ found in the biogas stream lowers the $H_2S$ level in the biogas to less than 50 ppm. This lower $H_2S$ concentration in the biogas and significantly reduces the operation and maintenance costs of the reciprocating engines in the AD system. Additionally, the high pH of the decanted liquid is now lowered to approximately 8.0 after neutralizing the acidic $H_2S$; resulting in a more friendly-to-use liquid for the farmer/owner and easier liquid disposal options.

As the impure biogas is bubbled through the effluent, impurities such as $CO_2$ and $H_2S$ are removed from the biogas by absorption into the effluent. Removal of the impurities is beneficial since this purifies or scrubs the biogas, making it more suitable for use. Absorption of $CO_2$ and $H_2S$ by the effluent is beneficial because it lowers the pH of the effluent to acceptable levels e.g. to about pH 8. Bubbling biogas through the ammonia stripping effluent is beneficial for both the effluent and the biogas.

Figure 3A:
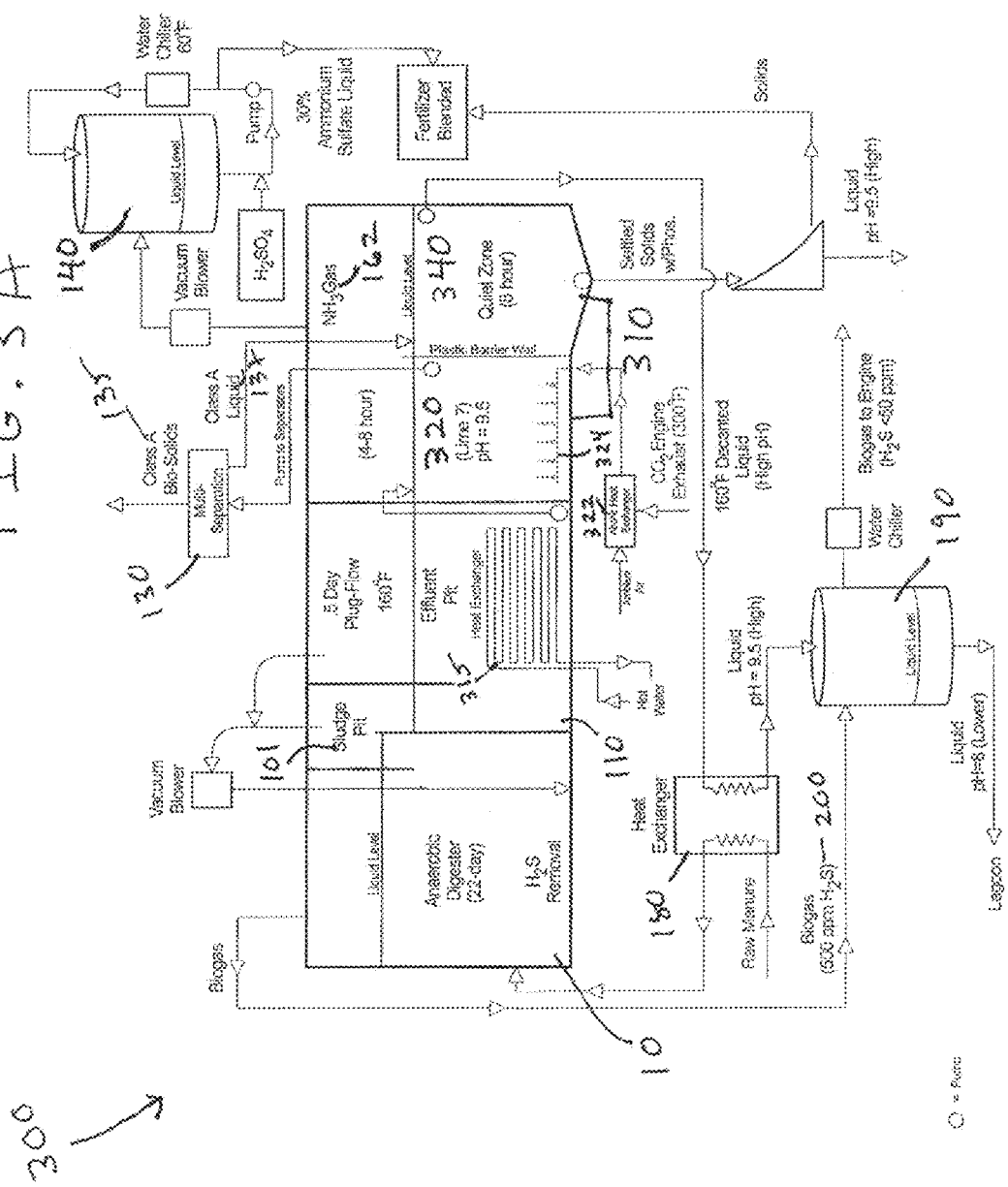
FIG. 3A is a schematic of one embodiment of a nutrient recovery system showing a two-chambered air-tight vessel.

FIG. 3A shows another embodiment of a nutrient recovery system 300. Nutrient recovery system 300 is similar to system 100, with some variations in the effluent pit (110) and a two-chamber air tight vessel 310 as opposed to a three-chamber air-tight vessel.

The nutrient recovery system 300 comprises an effluent pit 110 that comprises a heat exchanger 315 to heat the anaerobic digester effluent. The effluent pit also comprises a pump to transport the anaerobic digester effluent into the first chamber 320 of the two-chamber air-tight vessel 310.

The two-chamber air tight vessel 310 has a first chamber 320 that allows for the liquid stream to be gas-agitated with ambient air and $CO_2$ engine exhaust that is heated in a heat exchanger 322. In this example, the first chamber 320 serves as an aeration reactor.

Nozzles or jets 324 for injection of air into chamber 320 can be located at or near the floor of chamber 320. In another embodiment, the liquid stream may be hydraulic-agitated with a recirculation pump, or can be mechanically agitated with a prop agitation system. In an embodiment, the agitation can be for a suitable period of time including but not limited to 30 minutes to 1 hour, 1 to 2 hours, 2 to 4 hours, 4 to 6 hours, 6 to 8 hours, 8 to 10 hours, 10 to 12 hours, 12-18 hours, 18-24 hours, 24-36 hours, 36-48 hours, 48-60 hours, 60-72 hours and greater than 72 hours.

In an embodiment, the effluent is adjusted to a pH value ranging from 9.0 to 10.5. In an embodiment, a pH value of greater than 9.5 can be achieved by aeration, or aeration and the addition of an agent with a high pH value including by not limited to a caustic or quicklime. The addition of an agent with a high pH value can be used to increase the pH to a value of 9.5-10.0, 10.0-10.5, 10.5-11.0, 11.0-11.5, 11.5-12.0, 12.0-12.5, and greater than 12.5. The addition of an agent with a high pH value is optional and not required.

The effluent can be pumped to a multi-separator 130 that separates solids 135 from liquids 137. The solids and liquids meet the requirements to be considered Class A biosolids. The liquid effluent is pumped into chamber 340, which is a quite zone. The remaining components, recovery processes, and pH adjustments of the liquid effluent are essentially as described for system 100.

Figure 3B:
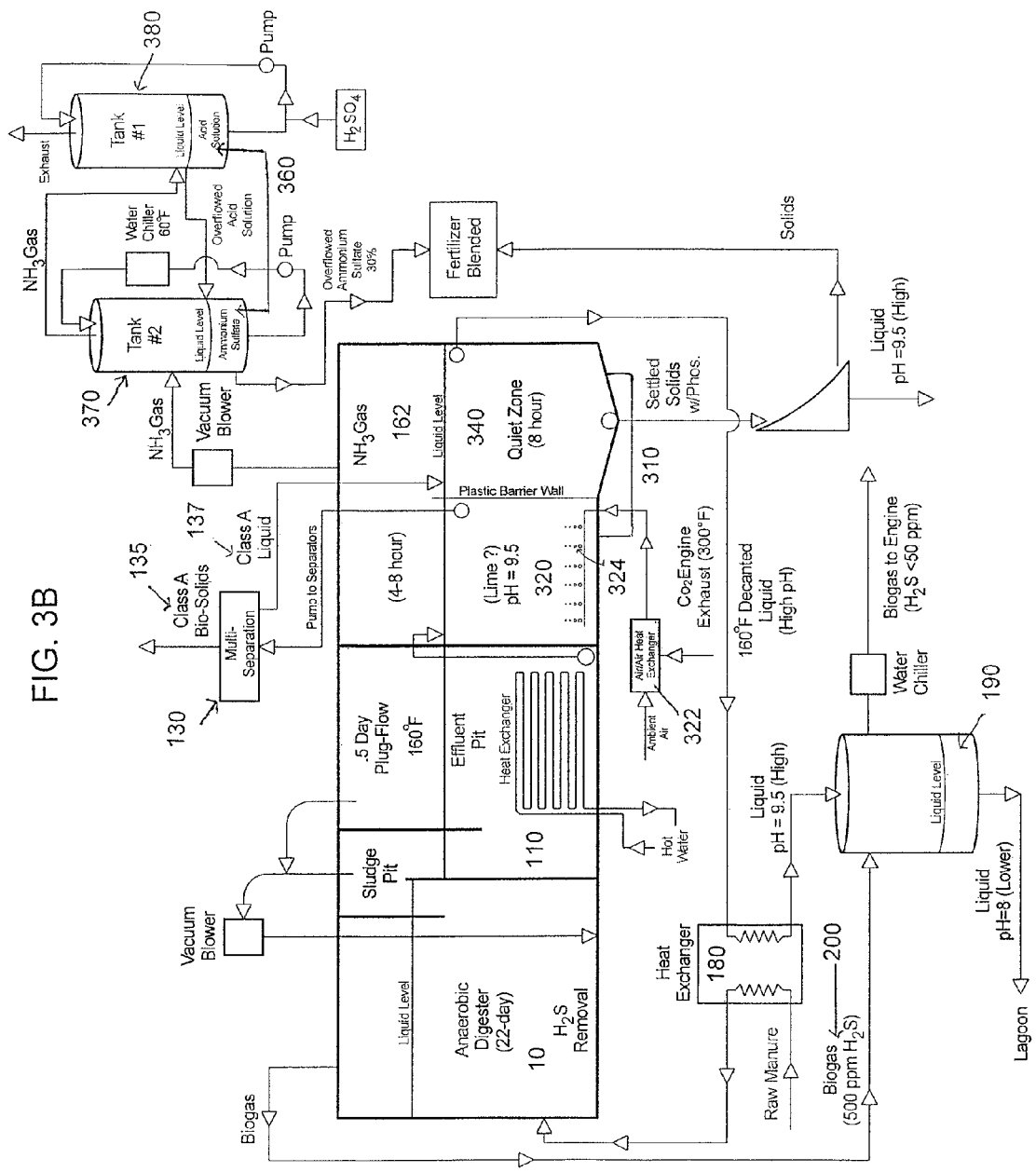
FIG. 3B is a schematic of one embodiment of a nutrient recovery system showing a stripping tower with a two tank system.

FIG. 3B shows another embodiment of a nutrient recovery system 305. Nutrient recovery system 305 is similar to system 300, with the exception that a two acid tower system is used (360). System 305 comprises inter alia an anaerobic digester 10, a sludge pit 101, an effluent pit 110, a separation device, 130, and a two chamber air-tight vessel 310, and a two acid tower system (360).

Anaerobic Digester

Any type of anaerobic digester (10) can be used as described above. In one embodiment, a mixed plug-flow through digester is used. In another embodiment, the digester has a retention time selected from the group consisting of 18, 19, 20, 21, 22, 23, 24, 25, 26, 27, 28, 29, 30, and greater than 30 days.

Effluent Pit

In one embodiment, the anaerobic digester effluent 20 can gravity flow, or it can be pumped, into an insulated effluent pit 110. In essence, the effluent pit is as described for system 100. In one embodiment, $CO_2$ and ammonia from the effluent pit is not pumped to the two acid tower system. Gas is pumped from the head-space of the effluent pit to a vacuum blower and back into the anaerobic digester. The re-circulated gas is used to circulate solids in the anaerobic digester.

In another embodiment, a stainless steel heat exchanger is used to heat the effluent and is supplied by a hot water tank for the digester. The effluent is heated to 160° F. in the effluent pit.

Air-Tight Vessel

The effluent is pumped from the effluent pit to a single chamber or multi-chamber air-tight vessel. A two chamber air-tight vessel 310 is shown in FIG. 3B. The first chamber 320 is separated from the second chamber 340 by a barrier wall.

In an embodiment, the barrier wall can be made of any suitable material that keeps the chambers distinct including but not limited to plastic PVC, polyethylene, polypropylene, methacrylic or acrylic plastic, fiber glass reinforced plastic (FRP), or stainless steel.

In an embodiment, the first and second chambers can be in any shape or dimension that allows the desired outcome including but not limited to a rectangle, a square, a triangle, a circle, a pentagon and a V-notched shape. One or more pumps can be located at or near the floor of the first and/or third chambers.

The First Chamber (320)

The first chamber 320 can have any desired shape or dimensions that achieve the desired result including but not limited to a rectangle, a square, a circle, a triangle, a pentagon and a V-notched shape. The first chamber 320 serves as an aeration reactor.

In the first chamber 320, the anaerobic digester effluent may be gas-agitated with ambient air that is heated in a heat exchanger (322) with the $CO_2$ engine exhaust. Aeration allows for release of the super-saturated gases, which impeded settling. Nozzles or jets (324) for injection of air into the first chamber can be located at or near the floor of the first chamber 320. In another embodiment, the liquid stream may be hydraulic-agitated with a recirculation pump, or can be mechanically agitated with a prop agitation system. In an embodiment, the agitation can be for a suitable period of time including but not limited to 30 minutes to 1 hour, 1 to 2 hours, 2 to 4 hours, 4 to 6 hours, 6 to 8 hours, 8 to 10 hours, 10 to 12 hours, 12-18 hours, 18-24 hours, 24-36 hours, 36-48 hours, 48-60 hours, 60-72 hours and greater than 72 hours.

In an embodiment, the liquid stream will have continuous agitation, which will aid in the removal of ammonia if removal is desired.

An agent with a high pH value can optionally be added. The agent includes but is not limited to quicklime or a similar caustic. The pH of the liquid effluent can be increased to a suitable value including but not limited to 9.0-9.1, 9.1-9.2, 9.2-9.3, 9.3-9.4, 9.4-9.5, 9.5-9.6, 9.6-9.7, 9.7-9.8, 9.8-9.9, 9.9-10.0, 10.0-11.0, 11.0-12.0, 12.0-12.5, and greater than 12.5.

The liquid stream will plug flow through the first chamber 320 of the air-tight vessel 310 as it is agitated utilizing the mixed plug flow (corkscrew) agitation method described above in the section entitled Anaerobic Digeters, and will thereby maintain a consistent HRT in the vessel.

Increasing the pH of an anaerobic digester effluent to a pH of about 9.5 or higher, at a temperature of 140° F. or greater, will convert soluble ammonium-nitrogen ($NH_4$—N) to non-soluble, volatile ammonia nitrogen ($NH_3$—N). The ammonia-nitrogen 162 will be volatilized rapidly with the continuous agitation provided in the air tight vessel and will be collected in the head space provided in the vessel. Vacuum extraction of the head space gases will be utilized to further increase the volatilization rate inside the air tight vessel.

In another embodiment, the aeration reactor comprises a heat exchanger to heat the air. An air-to-air heat exchanger will scrub hot air coming from the exhaust side of the stripping towers and heat fresh air that will be at ambient temperature. After going through the air-to-air heat exchanger the hot air will go through a roots-style blower (also increasing the air temperature) and be pumped to the diffusers in the aeration tank. A mixing valve is installed between the blower and the air-to-air heat exchanger that will operate off of a temperature probe that is downstream of the blower. This mixing valve will allow the air-to-air exchanger to be bypassed when the air is too hot to be supplied to the diffusers.

In another embodiment, condensation in the ammonia gas that comes out of the aeration tank is controlled by insulating the gas line between the aeration tank and the stripping towers. In addition, the stripping towers can be insulated as well as the gas line from the stripping tower to the air-to-air heat exchanger. In another embodiment, the gas line can be designed to slope toward the aeration tank before going straight down into the stripping tower. This design will help to ensure that if there is any condensation, it ends up back in the aeration tank and not the stripping towers.

Figure 3D:
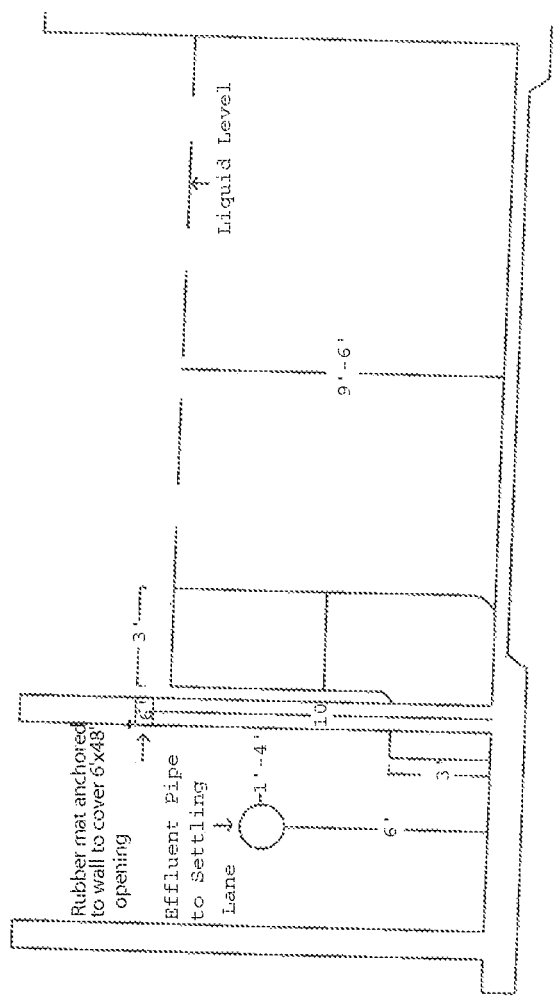
FIG. 3D is a representative schematic of an aeration reactor. The schematic depicts a view from the north elevation.
Figure 3C:
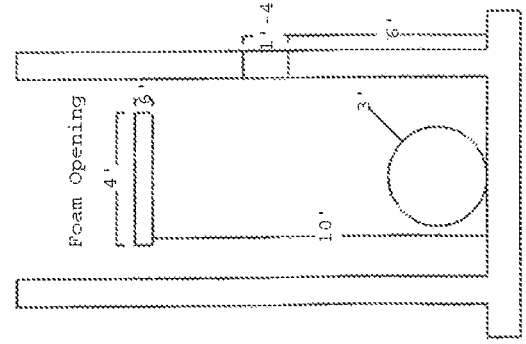
FIG. 3C is a representative schematic of an aeration reactor. The schematic depicts a view from the east elevation.

In still another embodiment, the outlet of an aeration reactor is a vertical pipe that comes down to a 90 degree elbow at the bottom of the tank and goes through the wall into a pump well. 6" above the top of that vertical pipe is a 4'×6" opening that foam can flow out of if it builds up inside the tank (FIG. 3C and FIG. 3D). There is a 15" pipe that carries effluent and/or foam to the settling lane. A perforated screen on the 4'×6" opening can be used to break up the foam. In addition, a ramp on the outside of the pump well can be provided where the foam can flow directly from an opening in the pump well to the settling lane. This opening will allow just foam to escape while effluent flows through the 15" pipe. Finally, if necessary, a pump can be installed in the pump well that sucks effluent from the bottom of the pump well and sprays the top, breaking up the foam.

FIG. 3C shows the foam opening and the outlet of a 36" chimney pipe into a pump well. The foam opening is 6" higher than the top of the chimney pipe and is there to allow foam that builds up in the aeration tank to flow to the pump well where it can be managed. The effluent pipe to the settling lane in the North wall of the east elevation is the outlet for the foam and effluent from the aeration tank. It gravity flows from there to the settling lane.

FIG. 3D displays the pump well on the left and aeration tank on the right. The chimney pipe takes liquid from the top of the aeration tank and allows it to flow to the bottom of the pump well. The foam opening is 6" above the top of our chimney pipe.

Solid/Liquid Separator

At the end of the engineered HRT, the anaerobic digester effluent will be pumped from the first chamber (320) to a solids/liquid separator 130; resulting in a separated solids 135 stream that will meet Class A bio-solids criteria and a separator liquid stream 137 that will also be sterilized and pathogen free. The separated solids and separated liquid will be reduced in ammonia-N content. The ammonium sulfate created will be a higher-value utilization of the natural ammonium found in organic wastes and will be in a chemical form that is easier to utilize and market. The separated solids can be utilized for animal bedding, horticultural usage, or fertilizer. The Class A liquid is pumped back into the head-space of the air-tight vessel (310).

Two Tower Stripping System

The system that is used for ammonia stripping may be of any suitable design. For example, a two-tower system may be used. In the two tower system, a first tower is used for ammonia stripping. The waste water effluent is injected near the top of the first tower. Air is directed into the bottom of the first tower using a fan or blower. The air accumulates volatilized ammonia and, with the pressures developed by the fan or blower, is sent to the bottom of the second tower. This ammonia enriched air is blown upward as acid is sent from the top of the second tower down through the media, absorbing the ammonia from the air. The resulting air, now ammonia free is returned back to the bottom of the first tower for continuation of the process. In this example, the acid injected into the second tower is sulfuric acid but it can be any acid that can combine with ammonia to form an ammonia salt In one embodiment, heat is supplied by excess generator heat from the AD process. However, in a preferred embodiment of the invention, the air is not directly heated, but instead is indirectly heated through the continual input of 30-35° C. manure wastewater coming from the anaerobic digester process, and is re-circulated and re-used continually. The air enters the bottom of the stripping section and flows upward, absorbing gaseous ammonia while moving toward the top of the ammonia stripping section of the tower. The action of the flow coupled with the use of a blower or fan sends the ammonia saturated air into an acid section of the tower. In one embodiment, the acid section contains sulfuric acid and, as the ammonia saturated air flows through the acid, the ammonia reacts with the acid to form an ammonium sulfate solution, which is removed. The resulting ammonia depleted air is then circulated back to the stripping section to accumulate additional ammonia, and so on. The result is a continuous, closed system whereby the same air can continually be used to absorb and release ammonia over and over again, resulting in significant cost savings in regard to electricity and heating.

Conventional ammonia stripping systems are not designed to deal with the usual amount of solid matter in an anaerobic digester effluent. Whereas the acid absorption tower (two-tower system) or the acid absorption portion of the tower in a single tower system may employ conventional small packing material in order to take advantage of its high efficiency, the anaerobic digester effluent may tend to clog small packing material in the ammonia stripping section. The stripping towers described herein may therefore be specially designed to solve this problem, and the tower design may be tailored to accommodate the particular type of animal waste that is being treated.

In one embodiment, a traditional tower is used but it is packed with coarse packing material and a relatively short packing height is used. For example, a tower with an inner diameter of 4" with a 1" pall ring and a packing height of 5' may be utilized with a feed flow of up to at least about 10 g/L of TS. In general, plastic packing material with a nominal diameter no less than 2" and a specific area of 80-120 $m^2/m^3$ may be used. Although smaller packing material or packing material with higher specific surface area will be better for mass transfer, it will be more easily clogged. A lower packing height (3-5 m) compared with the conventional 6.1-7.6 m is also preferred in order to reduce clogging.

In another embodiment, a tray tower with specially designed anti-clogging trays may be employed. The tray can be substantially flat and contain one or more gas guiding holes, and, optionally, one or more additional holes, which permit the flow of air and liquid through various trays. The gas guiding holes include a spaced apart cover that protects against the packing material in the tower from sealing off the gas guiding holes. Furthermore, the cover is opened in a direction desired for movement of gas and liquid. The tray may be of any suitable shape for example, substantially round, square etc. so long as the trays properly fit into and can be stably attached within the tray tower.

Returning now to FIG. 3B, $NH_3$ gas (162) in the head space of the air-tight vessel (310) will be piped to a two-tower acid system (360), where controlled amounts of sulfuric acid make contact with ammonia in the air and produce dissolved ammonia sulfate bio-fertilizer. $NH_3$ gas (162) is piped into tank two (370) of the two-tower system (360). Sulfuric acid is pumped into tank 1 (380) of the two tower system (360). Overflow acid solution is piped into tank two (370), which is mixed with $NH_3$ gas from the overhead space of the airtight vessel (310). Residual $NH_3$ gas is piped into tank 1 (380), and the circuit continues with overflow acid solution piped back into tank 2 (370). In this example, sulfuric acid is used but as discussed above, numerous types of acids can be used. The sulfuric acid will drop the pH of the air stream and create a solution comprising ammonium sulfate. The solution can comprise a ammonium-salt slurry comprising from about 30% to about 60% ammonium sulfate. The ammonium sulfate can be collected and used as fertilizer. The ammonium salt generated will depend on the acid used. For clarity, sulfuric acid is used in this example, but as stated previously, any suitable acid can be used, which will produce an appropriate ammonium salt.

Subsequently, by utilizing a system of air scrubbing the gaseous air stream with a low pH liquid solution of $H_2SO_4$ or similar acidic chemical, in a cross-flow two tower acid system 360, the ammonia will be removed from the air stream and captured as liquid ammonium sulfate. Ammonium sulfate is a highly valuable, easily solid fertilizer utilized by farmers and it will be an income stream for the nutrient removal system. Most importantly, the removal of the ammonium-nitrogen from the liquid waste stream solves one of the major disposal issues of the anaerobic digester effluent.

The Second Chamber

The liquid stream will plug flow into a second chamber 340, a "quiet zone" with no agitation where the liquid will be allowed to decant. The remaining solids will settle to the bottom of the second chamber, where they will be removed by a bottom discharge separation system. The aeration and high temperature that preceded the second chamber produces a high level of solids such as calcium and magnesium bound phosphates, and magnesium-ammonium-phosphate, which easily and readily settles. The settled solids will be removed from the second chamber 340 and dewatered.

In an embodiment, settling and dewatering of the nutrient rich solids is made easier through the use of a primary pump. In another embodiment, acid can be added to condense the solids layer for decanting.

Magnesium-ammonium-phosphate is also a highly valuable, easily sold fertilizer utilized by farmers and it will also be an income stream for the nutrient removal system. By removing the phosphorus and more ammonium from the liquid waste stream, the two largest disposal issues of the anaerobic digester effluent have been removed. The methods, systems and apparatuses disclosed herein contribute to solving many of the environmental and regulatory issues that generators/disposers of liquid organic wastes encounter in the US.

The remaining components including the heat exchanger of the nutrient recovery system 305 are as described for nutrient recovery system 100.

Figure 4:
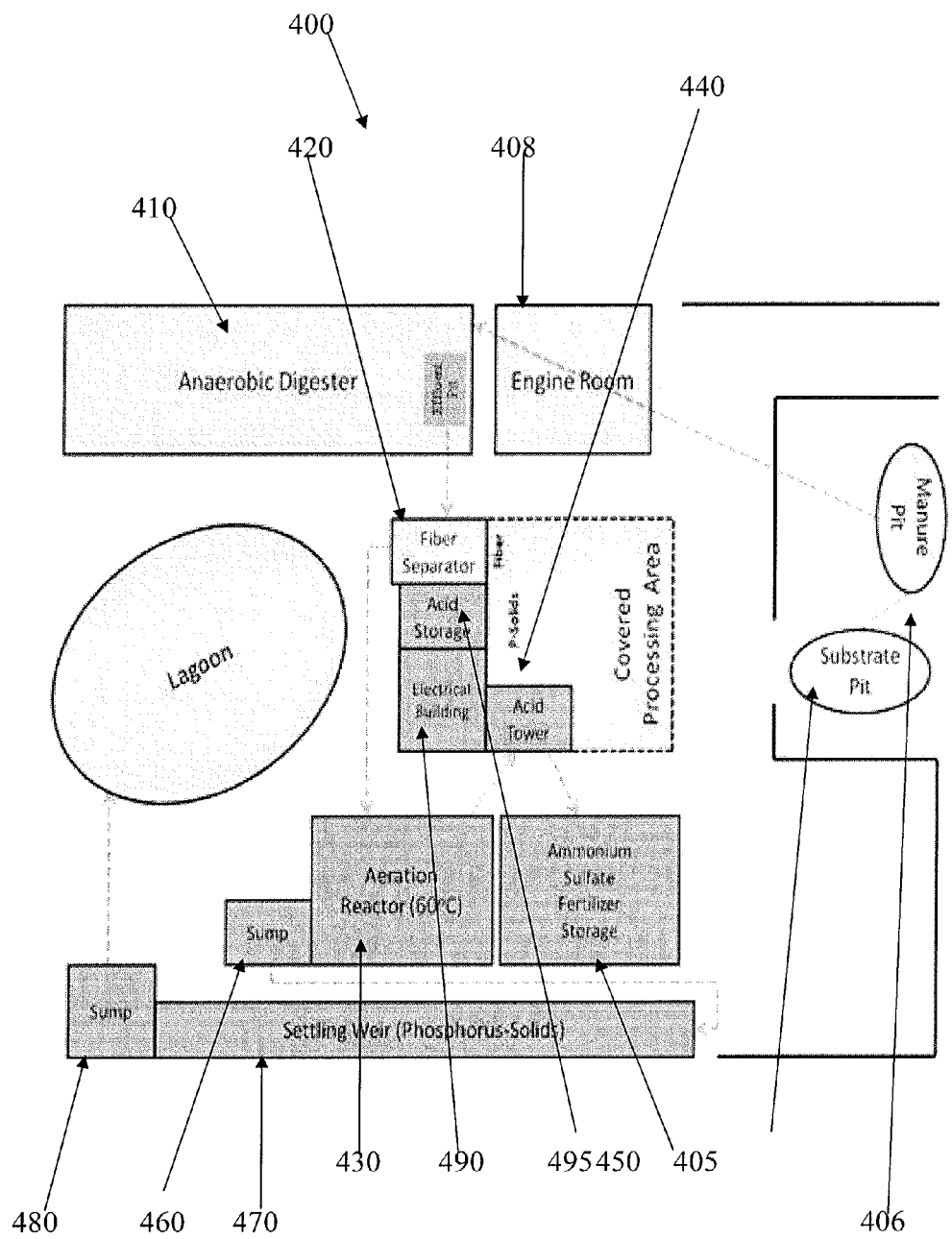
FIG. 4 is a schematic of one embodiment of a nutrient recovery system depicting one representative layout.

FIG. 4 shows an embodiment of a nutrient recovery system 400 depicting one possible layout of the system. Typically, a substrate pit (405) and a manure pit (406) would be present to retain waste material. The system 400 comprises an anaerobic digester (410). The waste material is transported from the manure pit (406) to an anaerobic digester (410). Waste is transported from the digester to the effluent pit, where material may be heated.

The system 400 also comprises a fiber separation chamber (420). The waste material is transported to a fiber separation chamber (420), where solids and liquids can be separated.

The system 400 also comprises an aeration reactor (430). The anaerobic digester effluent is transported to an aeration reactor where the effluent is heated to a suitable temperature including but not limited to 50-55, 55-60, 60-65, 65-70, and 70-80° C. The effluent is also aerated within the parameters discussed herein.

The system 400 also comprises an acid tower system (440) comprising two acid tanks. The acid tower system can comprise 1, 2, 3, 4, 5, or greater than 5 acid tanks. Aeration and increasing the pH shifts the equilibrium of soluble ammonium-nitrogen ($NH_4$—N) to non-soluble, volatile ammonia nitrogen ($NH_3$—N). The $NH_3$ gas is piped to the acid tower system, where controlled amounts of sulfuric acid make contact with ammonia in the air and produce dissolved ammonia sulfate bio-fertilizer (450).

The system also comprises a solids settling system, and as represented in FIG. 4, the settling system can be a settling weir (470). The settling weir (470) is a quiet zone that allows the solids to settle. A sump (460) pumps the effluent from the aeration reactor (430) to the settling weir (470). Phosphorous solids are collected from the settling weir.

Phosphate-rich solids may be removed from the AD effluent using any of a variety of known settling techniques. Depending on the type and condition of waste that is being treated, it may be advantageous to also carry out an initial mechanical separation (e.g. belt press, slope screen, etc.) step to remove large solids and particulate matter prior to solid settling.

Settling of solids may be carried out by any of several biological or chemical methods that are known to those of skill in the art. In one embodiment, a chemical procedure is used, examples of which include but are not limited to settling, flocculation, precipitation, electrocoagulation, struvite crystallization, etc. One method is settling in combination with flocculation.

Flocculation involves the removal of phosphate and other suspended solids through physical solid-liquid separation processes, such as sedimentation, screening, and filtration. These processes, without adding coagulant and/or flocculent polymers, generally have a low efficiency because the majority of the solids are in fine particulate form in manure wastewater. Brownian motion and fine particle mass produce very slow sedimentation of the colloid particles. Coagulants and flocculants can be used to enhance solid and phosphate removal by aggregating fine particles to facilitate rapid settling and screening. Common coagulants that may be used in the practice of the invention include but are not limited to inorganic compounds, such as aluminum sulfate (alum), ferric sulfate, and lime (CaO). Polyacrylamides (PAMs), which are high molecular weight long chain water-soluble polymers, may also be utilized.

The addition of coagulants and/or flocculants destabilizes the suspended charged particles and builds "bridges" between suspended particles, resulting in larger particle or floc formation that separates more easily from liquid effluent. In addition, most of the fine suspended particles in wastewater are negatively charged. The negative surface charge keeps the particles dispersed in wastewater due to electrostatic propulsion, resulting in stability of the particle suspension. The stability must be broken down before the particles can be aggregated, for example by the addition of polymeric cationic flocculants. Cationic polymers have numerous amine groups with strong positive charges, which neutralize the negative charges on the particle surface, and they may thus be used to neutralize the surface charges of fine particles in wastewater. Furthermore polymers may act as "bridges" between suspended particles and bridged particles interact with other particles resulting in an increase in floc size, thus enhancing settling of the particles.

Several types of cationic flocculants are suitable for use in manure effluent. These include but are not limited to polyethylenimines (PEIs), which comprise branched polymers with different molecular weights and positive charges, and strong cationic polymers such as the commercially available KlarAid PC.

In one embodiment, many of the solids are removed through settling, with the remaining P-rich solids being removed by flocculation using strong cationic polyamine polymers. Two polyamine polymers may be added to the effluent. The first is a cationic polymer of low molecular weight (MW) in the range of from about 3,000 to about 15,000. The chief goal of adding such a low MW polymer is to destabilize the negative particles by charge neutralization. The dosage of this polymer depends on particle content and charge density. In one embodiment, the particles still retain a weak negative charge after the addition of the low MW polymer. The second polymer is then added and is adsorbed onto the particle surfaces, thereby forming a large floc that will settle out of the effluent, or can be otherwise removed. The preferred MW of the second cationic polymer will be in the range of from about 0.7 million to about 2.0 million.

After solids have settled sufficiently from the anaerobic digester effluent, they are separated from the supernatant. This can be accomplished by any suitable means, e.g. by pumping the supernatant into a receiving tank and leaving the solids behind, or vice versa by pumping out the settled solids. The solids, which are in the form of a sludge, are rich in phosphorous, and may be recovered and used as fertilizer or in the preparation of fertilizer, with or without further treatment, e.g. drying, dewatering, etc. Dewatering of the solid precipitate (sludge) may be necessary in order to reduce the sludge volume and increase the liquid volume for ammonium nitrogen recovery. Any suitable means for carrying out this step may be employed, e.g. a screw or other type of press may be used for dewatering. As described above for other solids, dewatered sludge can be exported off the farm or sold as phosphorous rich fertilizer.

The system also comprises a sump (480) that pumps the effluent to the lagoon. In one embodiment, the effluent in the lagoon fulfills requirements to be considered a Class A liquid.

The system 400 can also comprise an electrical building (490) and an acid storage building (495).

The nutrient recovery systems can be modified and adjusted to contain some of the components above or equivalents of the components.

Nutrient Recovery Apparatus

Referring again to FIG. 4, a nutrient recovery apparatus can comprise a fiber separator (420), an aeration reactor (430), an acid tower system (440), and a solids settling system (470). The acid tower can comprise one or more than one acid tanks. The system can also comprise an anaerobic digester.

In another embodiment, the nutrient recovery apparatus can comprise ammonium salt storage apparatus (450). In another embodiment, the nutrient recovery apparatus can comprise an acid storage (495).

In an embodiment, an apparatus for the recovery of nutrients is provided. In one embodiment, the apparatus for recovery of nutrients comprises a single or multi-chambered vessel, pumps, vacuum blowers, pipes and similar devices to connect the components, and one or more apparatuses for containment of acid.

In one embodiment, the apparatus may contain a vessel partitioned into one or more than one chamber including but not limited to 1, 2, 3, 4, 5, 6, 7, 8, 9, 10 and greater than 10 chambers. In yet another embodiment, more than one nutrient recovery apparatus can be used simultaneously or sequentially.

In an embodiment, the chambers of the vessel may be of the same size, dimensions and shape. In another embodiment, more than one chamber of the vessel may be of the same size, shape and dimensions. In yet another embodiment, none of the chambers are of the same size, shape and dimensions.

In an embodiment, one or more than one chamber may have pumps located in the chamber. The pumps may be located at or near the floor of the chamber, or located at the sidewalls of the chamber or located near the ceiling of the chamber of located near the liquid level of the chamber. The pumps may be located at more than one location.

In one embodiment, the apparatus comprises a three-chambered vessel with a gas headspace above the liquid level and below the vessel ceiling. In an embodiment, the three-chambered vessel can be air-tight and operated under a vacuum. In another embodiment, all three chambers may be of different size, dimensions and shape. In yet another embodiment, two of the three chambers may be of the same size, dimensions and shape.

In one embodiment, the three chambered vessel comprises a first chamber with a pentagon or V-notched shape. The first chamber may be used to allow solids to settle. The first chamber is separated from the second chamber by a barrier wall.

In an embodiment, the second chamber is rectangular in shape, and comprises gas nozzles or jets for dispersion of gas including but not limited to air. The gas nozzles or jets can be located at or near the bottom of the second chamber. In another embodiment, the second chamber is used for adding an agent with a high pH value including but not limited to a caustic or quicklime. The second chamber is separated from the third chamber by a barrier wall.

In an embodiment, the third chamber has a similar size, shape and dimensions as the first chamber. The third chamber may be used to allow solids to settle and for collection of nutrient rich solids.

In one embodiment, the apparatus comprises a two-chambered vessel with a gas headspace above the liquid level and below the vessel ceiling. In an embodiment, the two-chambered vessel can be air-tight and operated under a vacuum.

In one embodiment, the two-chambered vessel comprises a first chamber. The first chamber may be rectangular in shape. In an embodiment, the first chamber of the two-chambered vessel may have gas nozzles or jets located at or near the bottom of the chamber floor. The first chamber of the two-chambered vessel may be separated from the second chamber by a barrier wall.

In an embodiment, the second chamber has a pentagon shape or a V-notch shape. The second chamber can be used to settle solids and for collection of nutrient rich solids.

In one embodiment, the headspace above the vessel is used for collection of $NH_3$ gas. The $NH_3$ gas can be pumped to a gas stripping tower with $H_2SO_4$ or nitric acid. The gas stripping tower can be used to produce an ammonium sulfate slurry comprising from 20% to 70& ammonium sulfate solids.

In another embodiment, the liquid effluent from the last chamber of the vessel (the chamber where nutrient rich solids are collected from) can be pumped to a heat exchanger. The heat from the liquid effluent can be used to heat raw waste materials in the anaerobic digester. The liquid, which has a high pH value, including but not limited to 9.0 to 10.0, can be passed through a gas stripping tower with biogas comprising $H_2S$. The biogas may comprise from 200 ppm to 600 ppm or from 300 ppm to 500 ppm $H_2S$. The gas stripping tower will produce a liquid effluent with a lower pH value including but not limited to 8.0 to 8.6, which can be used in multiple, safe applications. In addition, the concentration of the $H_2S$ in the biogas will be reduced to a suitable value including but not limited to 15-25 ppm, 25-45 ppm, 45-55 ppm, and 55-100 ppm. In an embodiment, the biogas comprises $H_2S$ at a concentration of less than 50 ppm.

The invention is now described with reference to the following Examples. These Examples are provided for the purpose of illustration only and the invention should in no way be construed as being limited to these Examples, but rather should be construed to encompass any and all variations that become evident as a result of the teaching provided herein. All references including but not limited to U.S. patents, allowed U.S. patent applications, or published U.S. patent applications are incorporated within this specification by reference in their entirety.

EXAMPLE 1

During anaerobic digestion, significant amounts of $CO_2$ and even some $CH_4$ produced during the biological process can become dissolved and/or super-saturated within the effluent. The $CO_2$ in anaerobic digested effluent becomes super-saturated because the $CO_2$ partial pressure of air is less than that of biogas in the anaerobic digester. These $CO_2$ bubbles are hard to escape from manure because too much suspended solids are contained within. The supersaturated gases interfere with the natural flocculation and settling process. Moreover, the existence of $CO_2$ bubbles in manure utilize a fraction of water to form gas-water layer, which will increase the electrostatic repulsive force of the particles in manure and make the solids even harder to settle down.

Figure 5A:
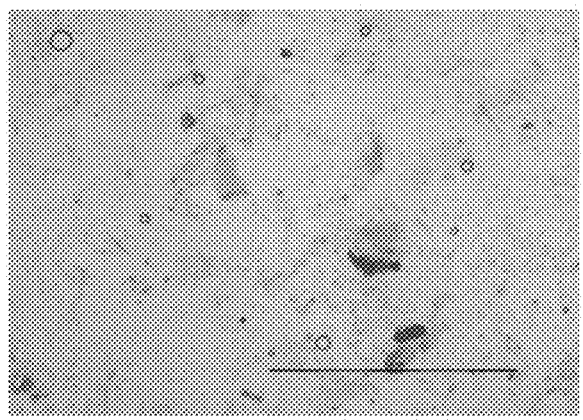
FIG. 5A is a photograph depicting gas bubbles in effluent.
Figure 5B:
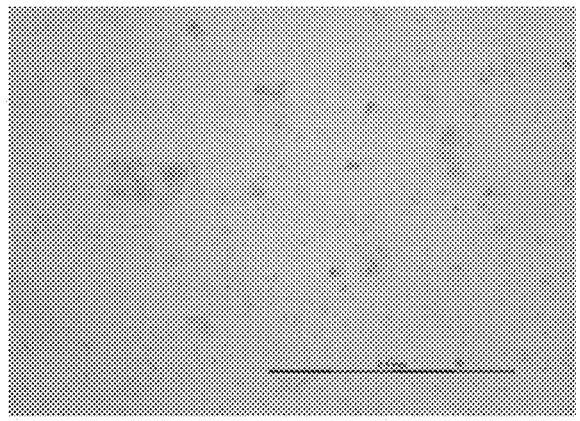
FIG. 5B is a photograph of effluent after aeration.
Figure 6:
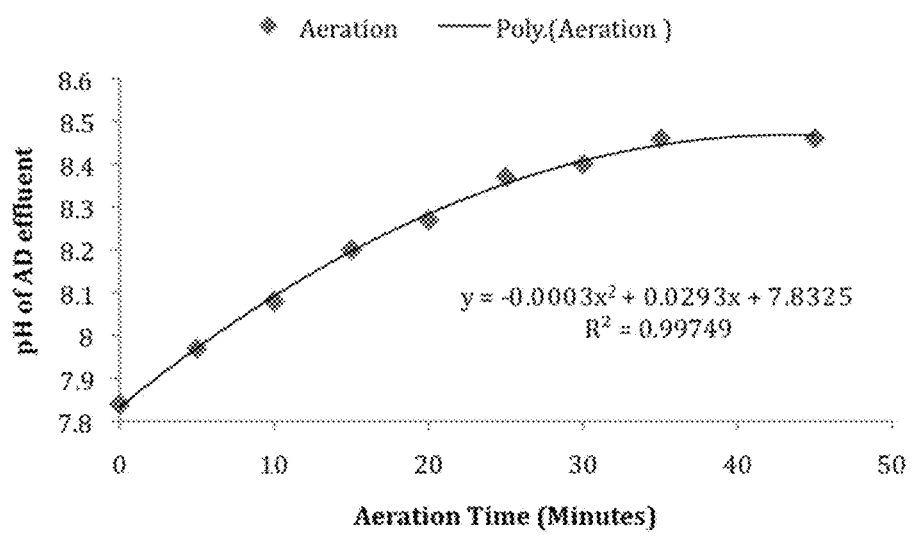
FIG. 6 is a line graph demonstrating the relationship between aeration time and pH of the effluent.

FIG. 5A depicts an image of micro-bubbles within liquid AD effluent, showing that these bubbles occur in numbers high enough to disrupt attractive forces with the buoyant forces and micro-turbulence they induce. The supersaturated $CO_2$ is released from the liquid in the form of fine bubbles. After 40 min aeration with 50 ml/min air through 200 ml anaerobic digested manure, the fine $CO_2$ bubbles disappeared (FIG. 5B). Aeration can remove the $CO_2$ bubbles in manure and increase the pH of manure (FIG. 6). During aeration, supersaturated $CO_2$ is released from liquid to gas phase.

In addition, analysis of chemical equilibriums shows that aeration releases the gaseous $CO_2$, the reactions move toward the right, generating more OH– and raising the pH of the solution, especially with elevated solution temperature. This process is summarized in Equations 7-12 below.

$$CO_2(aq) \rightarrow CO_2(g) \text{ increases} \quad (7)$$

$$H_2CO_3 \rightarrow H_2O + CO_2(aq) \quad (8)$$

$$HCO_3^- + H_2O \rightarrow H_2CO_3 + OH^- \quad (9)$$

$$CO_3^{2-} + H_2O \rightarrow HCO_3^- + OH^- \quad (10)$$

[OH—] increase causes pH to increase (11)

$$NH_4^+ + OH^- \rightarrow NH_3 \text{ increase} + H_2O \quad (12)$$

Figures 7, 8:
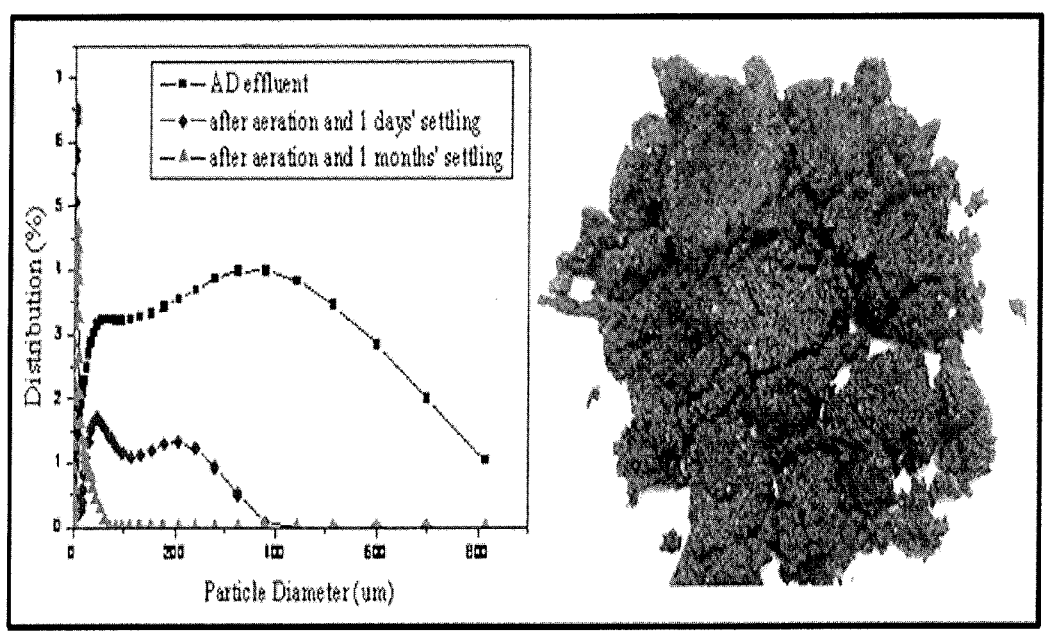
FIG. 7 is line graph depicting the ability for aeration and subsequent settling to more effectively settle solids and therefore phosphorous as compared to no aeration.
FIG. 8 is a photograph of settled phosphorous-solids removed from a solids settling system.

Subsequent testing of this high temperature aeration process verified that the stripping of the $CO_2$ and corresponding elevation in pH also allowed for enhanced ammonia stripping and P-settling without chemical addition. As shown in FIG. 7, aeration followed by a period of settling allowed for efficient recovery of phosphorous. FIG. 8 is a photograph of settled phosphorous solids from a solid settling system, in this case a settling weir. Thus, aeration treatment not only leads to the desired phosphorous-settling but also nitrogen removal through the stripping and assumed recovery of the ammonia—yielding an integrated nutrient recovery process with vastly reduced chemical inputs.

Removal of interfering gases led to significant improvement in settling capability and solids/phosphorous removal. Without aeration, only 28.4% of TP was settled during a 24 hour period. In contrast, aeration and a subsequent 24 hour settling period achieved 52.3% TP removal. In an effort to further improve the performance without too much additional cost, an additional step comprised of lime addition was completed. Table 1 summarizes the results of the different sequential steps, ultimately leading to a nearly 80% TP removal through a combination of aeration, lime addition and 24 hour settling. This performance compares favorably with coagulant/polymer/belt press (AL-2 technology) operation but with significant reductions in chemical and energy inputs while also preserving a fibrous product for use as bedding and/or value-added sales.

TABLE 1

TP removal percentages with aeration, lime treatment and settling

| AD Effluent-Fiber TP (mg/l) | Settling for 24 h | | Aeration for 40 min and settling for 24 h | | Aeration/lime (2 g/l), settling 24 h | |
|---|---|---|---|---|---|---|
| | TP (mg/l) | TP removal (%) | TP (mg/l) | TP removal (%) | TP (mg/l) | TP removal (%) |
| 1760 | 1260 | 28.4 | 840 | 52.3 | 380 | 78.4 |

$$Ca(OH)_2 \leftrightarrow Ca^{2+} + 2OH^- \quad (4)$$

$$HCO_3^- + OH^- \rightarrow CO_3^{2-} + H_2O \quad (5)$$

$$H_2CO_3 + OH^- \rightarrow HCO_3^- + H_2O \quad (6)$$

EXAMPLE 2

It is believed that during anaerobic digestion significant amounts of $CO_2$ and even some $CH_4$ produced during the biological process can become dissolved and/or super-saturated within the effluent. This is particularly true of $CO_2$ that is stored within the liquid effluent as $CO_2(aq)$, $H_2CO_3$, bicarbonates and carbonates. Upon release from the digester, changes in temperature, pressure, pH, air and agitation can lead to a release of these super-saturated gases. As the $CO_2$ partial pressure in air is much lower than that inside a digester, a hypothesis was proposed that aeration would remove the dissolved $CO_2$ and enhance P removal. Through aeration, the dissolved $CO_2$ becomes supersaturated.

Analysis of chemical equilibriums shows that as aeration releases the gaseous $CO_2$, reactions move towards the right, generating more OH$^-$ and raising the pH of the solution, especially with elevated solution temperature (FIG. 9A). Subsequent testing of this high temperature aeration process verified that the stripping of the $CO_2$ and corresponding elevation in pH also allowed for enhanced ammonia stripping and P-settling without chemical addition (FIG. 9B and FIG. 9C). Thus, aeration treatment not only leads to the desired P-settling but also N removal through the associated stripping and assumed recovery of the ammonia fraction of the N in the effluent—yielding an integrated nutrient recovery process. Notably, the process requires no chemical input, instead relying solely on aeration and temperature, both which can be supplied using only engine exhaust heat and parasitic electricity.

EXAMPLE 3

Aeration for pH control and phosphorous-rich solids settling was evaluated at Big Sky Dairy in Goodnig, Id. on a 4,700 cow farm. Table 2 summarizes the laboratory and pilot data obtained using Big Sky manure for the purpose of P-removal and recovery without aims towards ammonia recovery or enhanced temperature treatment. These TP removal rates do not incorporate the TP removed from wastewater due to fiber removal, which can add an additional 5-10% removal.

TABLE 2

Big Sky laboratory and pilot-scale aeration results

|  | Aeration Rate gallons/cfm | Temperature °C. | Aeration Time Hours | TP Removal % |
|---|---|---|---|---|
| Big Sky Lab | 175 | 35 | 5 | 70 |
| Big Sky Pilot | 100 | 20 | 7 | 53 |

* Each experiment done with 24 hours of settling prior to testing of wastewater liquid TP In the laboratory experiments, a final pH of 9.1 was achieved and a TP removal of 70% while the Big Sky Pilot study achieved a pH elevation of 8.7 and a TP removal of 53%. The difference likely is due to the lower aeration rate and the temperature of the manure during the aeration. It is believed, based on data not shown, that an increase in settling time from 24 hours, which was done in these studies, to longer periods of around 3 days can increase the TP removal by at least 5-10%. A system devised to aerate at more elevated temperatures as well as systems to increase the aeration time would likely increase the removal of total phosphorous.

Aeration may take place primarily in the anaerobic digester effluent pit where the temperature of the manure is still very near 35° C. It is anticipated that a combination of 7 hours of heated aeration with additional extended aeration at lower temperatures will allow for an equivalent raise in pH as was observed in the Big Sky laboratory results.

The data show that even at lower temperatures and low rates of aeration, TP removals of 50% are always attainable, while optimization to higher temperatures, high aeration rates, higher aeration times, and higher settling times can achieve 85% removal. Thus, for this particular system (to best fit with available infrastructure and design cost), the range of TP removal is somewhere between 50-85%. With modification to the planned limits in aeration rate, time, temperature and settling, TP removal is more likely between 60-70%. If the missing TP from fiber separation is included, total TP removal is planned to be in the range of 65-75%.

EXAMPLE 4

The effect of aerating the effluent, which was at a specific temperature, and the duration of settling, were evaluated to determine the effect on total phosphorous in the effluent. The analysis was performed at Big Sky Dairy in Goodnig, Id. on a 4,700 cow farm. Table 3 provides a summary of the results.

The total phosphorous in the effluent was evaluated with different aeration times and settling times. The aeration rate used was 0.01 cfm/gallon. A larger blower could be used to increase the cfm. A sample with no aeration, and no settling served as the baseline, and resulted in a TP of 470 mg/L in the effluent. Settling for 24 hours, with no aeration resulted in a TP of 260 mg/L in the effluent, demonstrating the phosphorous had settled, and could be collected. Samples were aerated from 1 hour to 24 hours, with 24 hours of settling with the exception of one sample that was settled for 41 hours. The sample that was aerated for 24 hours with 41 hours of settling yielded a TP of 200 mg/L in the effluent, and a pH of 9.1. Increasing the settling time and the aeration time increased the pH value and also the recovery of the total phosphorous.

TABLE 3

Effects of aeration and settling on total phosphorous.

| Aeration | Temp (° C.) | Settling | pH* | TP (mg/L) | % Recovery |
|---|---|---|---|---|---|
| 0 hour | 27 | 0 hour | 8.1 | 470 | N/A |
| 0 hour | 27 | 24 hour | 8.4 | 260 | 44.6 |
| 1 hour | 27 | 24 hour | 8.4 | 230 | 51.1 |
| 2 hour | 27 | 24 hour | 8.4 | 220 | 53.2 |
| 3 hour | 27 | 24 hour | 8.5 | 200 | 57.4 |
| 4 hour | 27 | 24 hour | 8.6 | 210 | 55.3 |
| 5 hour | 27 | 24 hour | 8.6 | 210 | 55.3 |
| 6 hour | 27 | 24 hour | 8.6 | 230 | 51.1 |
| 7 hour | 27 | 24 hour | 8.7 | 220 | 53.2 |
| 24 hours | 27 | 41 hour | 9.1 | 200 | 57.4 |

*pH was recorded after cooling to 16° C. for more accurate measurement with pH probe

EXAMPLE 5

A major concern at the Big Sky Dairy in Goodnig, Id. is phosphorous control. Presently, the AL-2 technology developed out of Denmark is accomplishing some degree of phosphorous control, achieving near 80% total phosphorous removal from the AD wastewater. The AL-2 technology uses a combination of flocculants and polymers (optional chemical mix was 195 ml/m$^3$ alum with 1,250 ml/m$^3$ polymer for phosphorous removal.

Unfortunately, the process has two significant drawbacks. First, the system must retain the fibrous solids in the process, using them as a bulking agent to reduce chemical input needs. This results in the fiber being encased in a polymer/coagulant product after belt-press separation, which can be further treated via composting for potential sale as a soil product. Unfortunately, the fibrous solids are no longer available for use as farm bedding or as a potential value-added peat replacement as original Big Sky business plans envisioned. Second, the AL-2 process requires extensive use of chemicals and as such in not particularly environmentally friendly and incurs significant capital and operating costs to the farm.

Table 4 below summarizes the capabilities and costs of the AL-2 system as studied at Big Sky. About eighty-three percent (83.1%) TP reduction (including TP from fiber) was attained but at the cost of making fiber unavailable and requiring chemical input and electrical costs of $2.90/m$^3$ and $0.07/m$^3$, respectively or $2.97/m$^3$ total (~1¢/gallon treated). But this product is also less desirable for end users because of the inclusion of industrial chemicals and polymers and the loss of the available bedding. Therefore, a more realistic price for this process rises to about $6.95/m$^3$ or $0.026/gallon, due to loss of marketable fiber ($1.92/m$^3$) and additional compost treatment ($2.06/m$^3$).

TABLE 4

| Kemira/AL-2 commercial performance and cost analysis (100 gallons per minute) | | | |
|---|---|---|---|
| | TS Reduction (%) | TP Reduction (%) | TN Reduction (%) |
| Performance | 72.3 ± 3.0 | 83.1 ± 3.7 | 38.2 ± 2.4 |
| | Chemical Cost | Electrical Cost | Capital Cost |
| Cost Analysis | $2.90/m$^3$ | $0.07/m$^3$ | $80-100/cow |

Further studies were performed using pilot-scale decanting centrifuges using no inputs of chemical flocculants and/or polymers and marginal success (60% TP removal) was achieved. However, there was still high capital, operating, and maintenance costs associated with the system. In addition, the system was under-performing from the targeted 80% TP removal deemed necessary for many of our operating CAFO dairies.

In comparison, the methods, systems and apparatuses disclosed herein achieve at least 65-75% TP removal without interfering with the fiber/bedding production. In addition, there are no chemicals or associated chemical costs and an electrical cost of only $0.13/m$^3$, which is only 2% and 4% of the larger and smaller calculated AL-2 operating costs, respectively. Also, it is anticipated that the aeration treatment will reduce the ammonia odor of the fiber bedding, providing a small improvement to product quality.

EXAMPLE 6

Table 5 provides a summary of capabilities based upon laboratory data (1 L scale) using anaerobic digester dairy effluent (Big Sky Dairy, Id.). The parameters of the system were as follows: an aeration rate of 20 gallons/cfm, micro-aeration was used, the effluent was at a temperature of 70 C, aeration was performed for 2 hours and settling was for 48 hours.

Table 5 outlines the mean nutrient recovery performance of the entire anaerobic digester/nutrient recovery operation and its individual unit operations.

TABLE 5

Nutrient recovery potential of entire AD/NR system and its unit operations

| | Manure | Effluent | Post Fiber | NR Effluent | % Reduction |
|---|---|---|---|---|---|
| Total Solids (%) | 8.0 | 4.9 | 3.6 | 2.2 | 73 |
| Total Nitrogen (%) | 0.35 | 0.35 | 0.33 | 0.13 | 63 |
| NH$_4$ Nitrogen (%) | 0.17 | 0.22 | 0.22 | 0.04 | 77 |
| Total Phosphorus (%) | 0.080 | 0.080 | 0.072 | 0.014 | 83 |
| Coliform (cfu/g) | 339,031 | 3,418 | 944 | ND | 99.9 |

Values reported are means of n = 24 trials; Effluent refers to wastewater after 35° C. AD of 22 days, Post Fiber refers to effluent after mechanical separation of fibrous solids, NR refers to nutrient recovery, and ND is non-detectible Products include: (1) fibrous bedding at 74% moisture with 0.3% TP (DWB); (2) P-rich solids at 77% moisture with 2.5% TP and 4.0% TN (DWB); and (3) ammonia-salt slurry at 30% ammonia sulfate and 6.4% TN (DWB).

Through a unique combination of anaerobic digestion, mechanical separation of fibrous solids and subsequent nutrient recovery treatment, manure effluent stored on farms and applied to fields is significantly reduced in solids content, pathogens, ammonia nitrogen, total nitrogen and total phosphorous, with nutrient recovery representing the bulk of these improvements. The dairyman's total reduction of nutrients as a percentage is given in the last column. It is important to note that this is not just reduction but recovery and in more exportable and marketable forms.

The nutrients recovered leave the farm in the following forms:
  Phosphorous—some in the fiber and most in phosphorous-rich organic solids
  Nitrogen—some in the fiber but most in the form of ammonium sulfate slurry or salts; and
  Solids—some in carbon conversion to biogas, most either in fiber or in P-rich solids From a mass balance perspective, this amounts to the recovery and removal from overburdened farms of 97 kg N/cow yr, 57 kg NH$_3$/cow yr, and 29 kg P/cow yr with even greater mass recovery on farms practicing co-digestion. Importantly, some nutrients still remain in the effluent, offering dairy producers the opportunity to use their effluent as an on-farm fertilizer but with vastly reduced risk of air and water quality contamination and reduced risk of over-application on limited crop acreage. In addition, existing agriculture-based nutrients are more sustainably managed, moving from a system whereby manure-based nutrients are actively lost to the air in ammonia and treated as nuisance by-products to a system where nutrients are stabilized and more effectively transported to distant fields in need of fertilizer value.

Beyond, concentrating, recovering and potentially exporting a significant percentage of nutrients off of the farm in a more economically marketable form, the process also produces Class A solids and liquids, significantly reduces pathogen counts in the solids and liquid, reduces the ammonia odor of the separated fibrous solids, increases methane production by as much as 10%, and assists in lowering hydrogen sulfide content within the biogas to near or below 50 parts per million. Inputs to accomplish all of this include waste engine exhaust heat and only small amounts of acid to produce the ammonia sulfate salt—vastly lowering input and operating costs as compared to other nutrient recovery systems which utilize other standard wastewater processing technologies (i.e. flocculants and polymers).

EXAMPLE 7

Figures 10A, 10B:
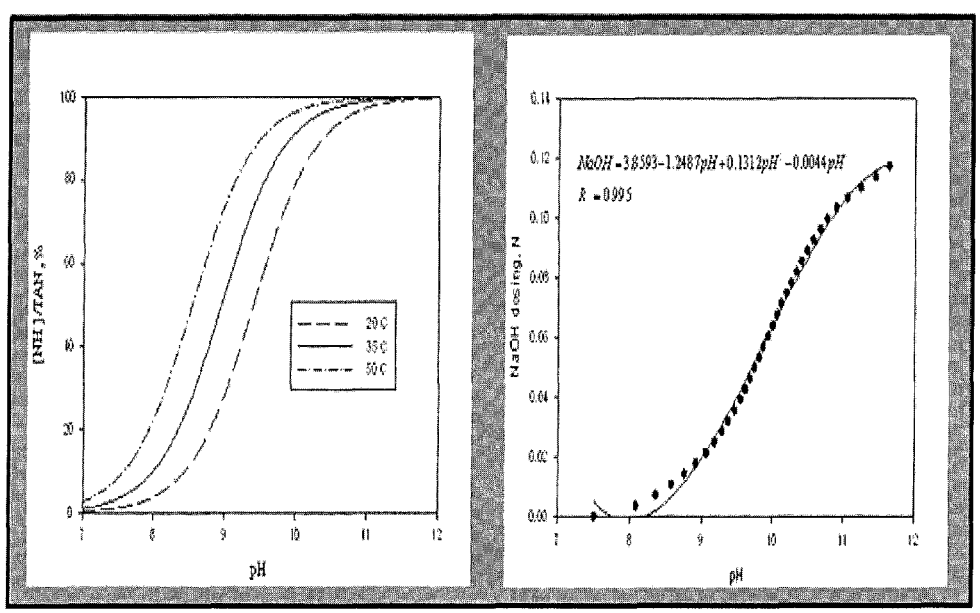
FIG. 10A is a line graph reporting the optimal pH range for free ammonia release from anaerobic digester effluent.
FIG. 10B is a line graph depicting an alkali dosage curve for attainment of the optimal pH for release of ammonia from anaerobic digester effluent.

The removal of ammonia from the anaerobic digester effluent can be enhanced by elevating the pH. As FIGS. 10A and 10B highlight, elevation of 35° C. anaerobic digester effluent pH to near 10.0 allowed for a significant shift in ammonia equilibrium in favor of gaseous or free ammonia, required for stripping. The high buffering capacity of anaerobic digester effluent required a significant amount of alkali material (lye or lime) to raise the pH to that desired level. Pilot studies showed the need for an input of 10-11 kg lime/m$^3$ anaerobic digester effluent at a cost of roughly $1/m$^3$.

EXAMPLE 8

One revenue mechanism, which holds potential for assisting CAFO operators on important regulatory concerns related to nutrient management and control of air and water quality emissions, is recovery and export of nitrogen and phosphorous, in the form of saleable bio-fertilizers. CAFO operators who install an anaerobic digester unit at high capital cost to their farm, yield potentially significant gains but importantly, the anaerobic digester process does little to improve upon their concerns with nutrient overloads, particularly if they are practicing co-digestion. This is because anaerobic digestion is in essence a carbon management tool, in-part converting organic material to inorganic carbon compounds (methane and carbon dioxide), thus gasifying a portion of the carbon and removing it from the farm. The same cannot be said for nitrogen and phosphorous. While the anaerobic digestion process in-part converts nitrogen and phosphorous from organic to inorganic form, the conversion maintains these macro-nutrients within the liquid or solid state, and as such the AD effluent after application to fields, still represents a source of over-loading nutrients to limited farm acres. From a CAFO perspective then, adoption of AD technology would be much more attractive if both nitrogen and phosphorous could be economically extracted from the effluent.

Figure 11:
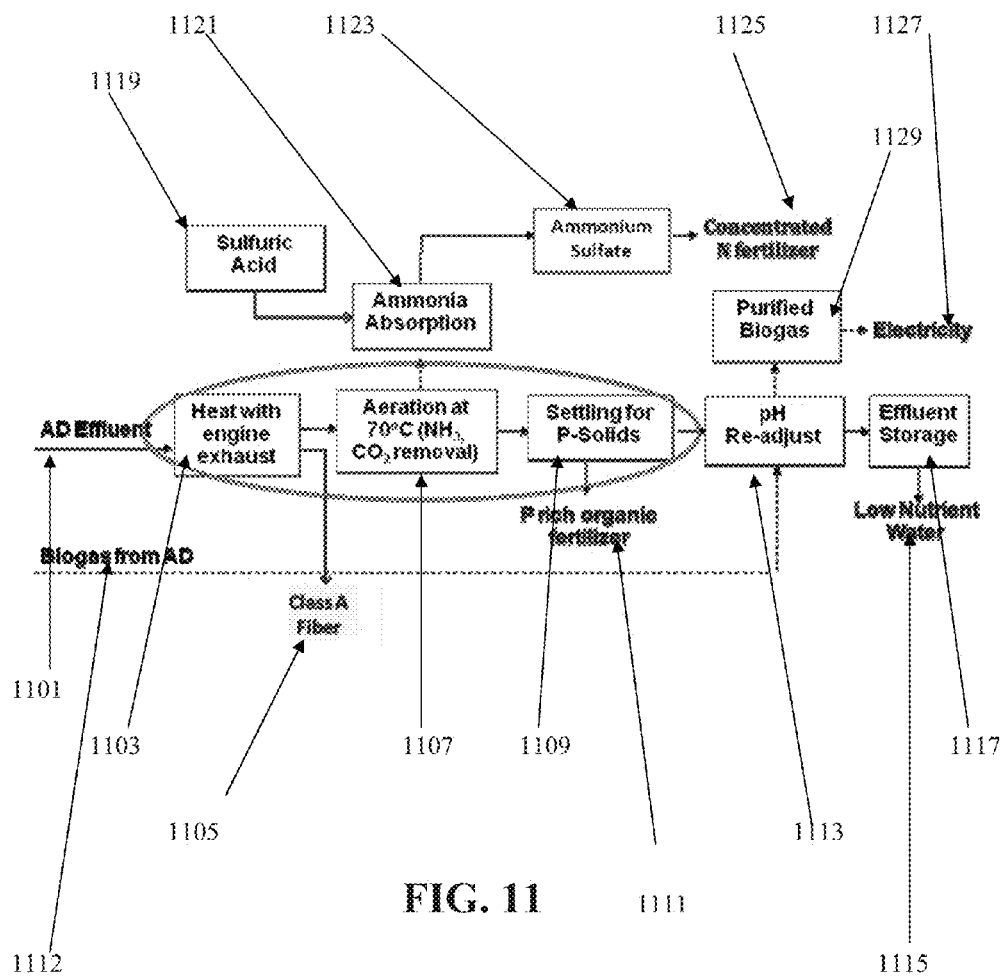
FIG. 11 is a schematic depicting a commercial, economically viable approach to the recovery of a nutrient from an anaerobic digested effluent.

FIG. 11 provides a schematic of a system for recovery of nutrients from anaerobic digestion effluent. Waste engine heat (1103) from the AD engine/generator sets is used to heat anaerobic digester effluent (1101). The temperature is raised to 70° C. and the effluent is aerated (1107). Aeration can be achieved using micro-aerators using $CO_2$, biogas, a liquid, a gas, or a combination of $CO_2$ and biogas. The aeration rate can be any suitable rate including but not limited to 0.1-1,1-5, 5-10, 10-15, 15-20, 20-25, 25-30, 30-35, 35-45, 45-55, 55-60 and greater than 60 gallons/cfm.

The effluent is heated for the necessary time duration to meet EPA Class A solids standards, thereby producing a more valuable and highly controlled pathogen-reduced fiber for bedding or off-farm sales. In addition, the aeration and increased temperature induce degassing of super-saturated $CO_2$ and the release free ammonia. After aeration, the treated effluent is sent to a quiescent zone to allow for settling and removal of P-solids in a weir system (1109). Phosphorous-rich organic fertilizer can be collected (1111).

After aeration at the elevated temperature, $CO_2$ and $NH_3$ enter the headspace and with the assistance of a partial vacuum pump can exit the aeration tank (1107) and enter a two-tower acid contact system (1121), which allows the ammonia to react with concentrated sulfuric acid at controlled pH to produce soluble ammonia sulfate (1123). Due to the high reactivity of the ammonia with the acid at low pH and the corresponding low reactivity of the $CO_2$, nearly 100% of the accumulated ammonia is reacted to a salt form with $CO_2$ exiting through the exhaust of the system. A two tower acid system allows for pH adjustment in the second tower as well as development of an overflow solution tank at a controlled maximum of concentration (~40% depending upon liquid temperature). With some in-line filters placed in the overflow piping, the result is a neural pH product with consistently high 40% by mass concentration of ammonia sulfate, containing a minimum of solid impurities.

Effluent leaving the aeration (1107) and settling zones (1109) is still at a relatively high pH (~9), so prior to storage in lagoons and application to fields, it is deemed important to return the solution back to neutral. Within the integrated system, this can be accomplished by designing a second contact tower (1113) that allows for controlled reaction between raw biogas from the digester (1112) and the high pH effluent. Raw biogas contains acidic compounds, which both lower the BTU value ($CO_2$) and the engine-friendliness ($H_2S$) of the fuel.

In particular, anaerobic digester suppliers have been actively researching methods to gain better control on $H_2S$ emissions and minimize their effect on engine maintenance, beyond using the industry standard of running the engine lean with intensive oil replacement. Within this contact tower (1113), the acidic compounds readily leave the gaseous state and dissolve within the liquid, lowering the pH to near neutral and more acceptable levels.

Figures 12A, 12B:
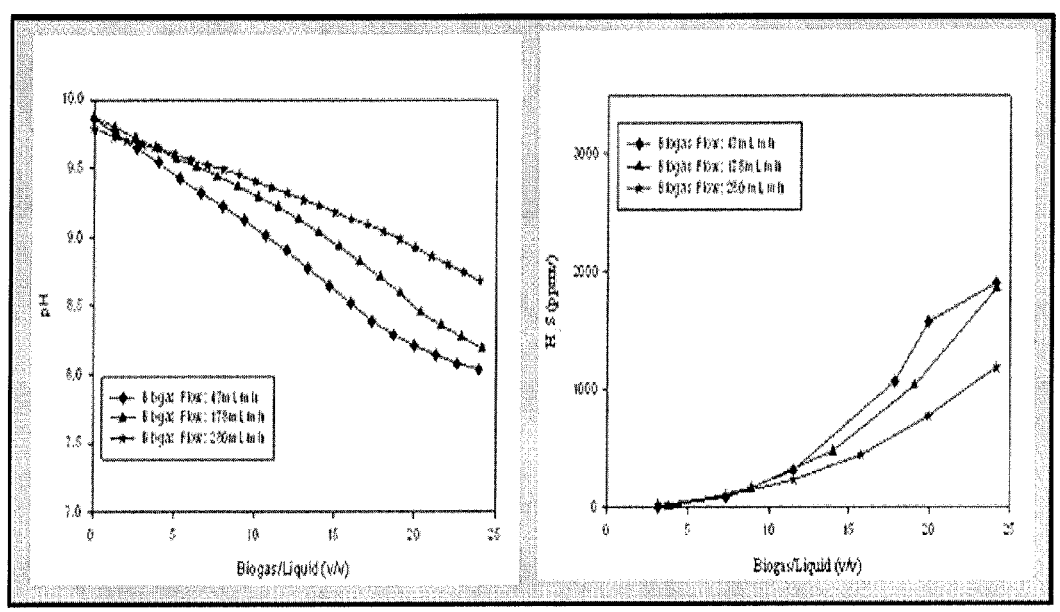
FIG. 12A is a line graph depicting the response of lowered pH through biogas/liquid contact.
FIG. 12B is a line graph depicting selective $H_2S$ removal through contact time manipulation.

As shown in FIG. 12A, the lowering of the pH was a result of both the high solubility and acidity of the gaseous impurities and the high gas to liquid ratios (~25:1) found in typical manure digesters. As typical biogas streams are composed of as much as 35-40% $CO_2$ and only 1,000-3,000 ppm $H_2S$, a majority of the $CO_2$ entered the liquid stream, and lowered the pH. Further analysis did show that selective removal of $H_2S$ in lieu of $CO_2$ is possible through manipulation of contact time, flow rate, liquid height, and bubble size (FIG. 12B).

EXAMPLE 9

Figures 13A, 13B:
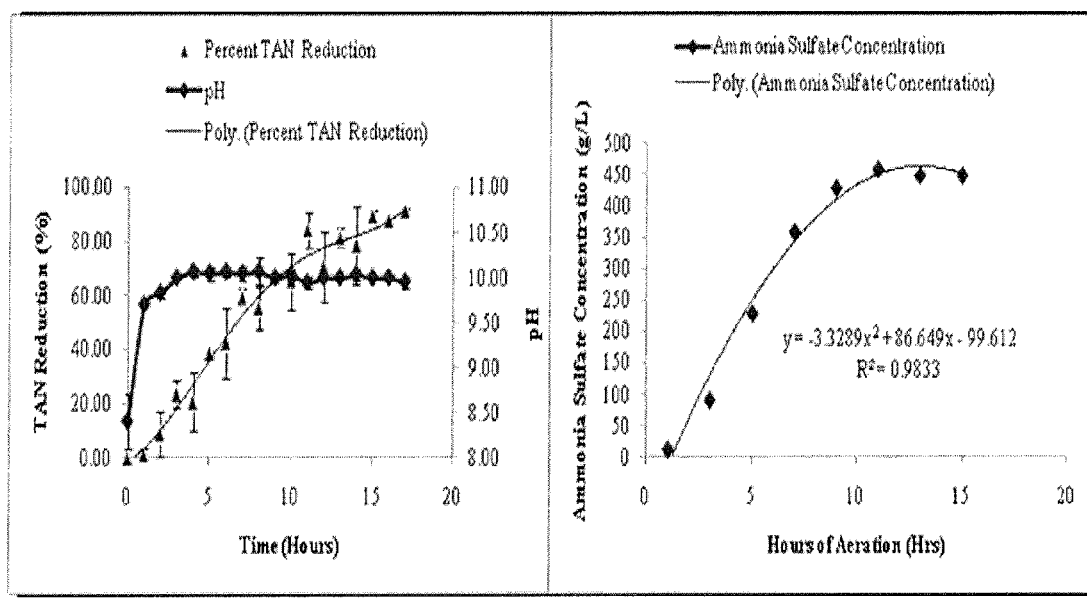
FIG. 13A is a line graph depicting the performance capabilities of ammonia stripping at specified aeration conditions and temperature.
FIG. 13B is a line graph depicting the performance capabilities of ammonium sulfate recovery at specified aeration conditions and temperature.

Aeration and heating of the anaerobic digester effluent are key components of the nutrient recovery system. The aeration flow rate was set at 20 gallons/cfm (micro-aerators) and the temperature was maintained at 55° C. The results are described in FIGS. 13A and 13B, which suggest the use of longer retention times, most likely due to lower operating temperatures (limited availability of waste heat energy and losses of heat due to mechanical separation of fibrous solids) and lower mass-transfer due to mixing limitations at larger scale (foaming). The above aeration rate and temperature minimize energy inputs and controlled foaming while still stripping ammonia in a reasonable retention time. At the aforementioned optimized parameters, nearly 80% of TAN was stripped during a 15 hour operation due to a consistent capability to raise the pH at or near 10.0. The two tower acid contact system, once equilibrium at maximum solubility was attained, produced a consistent 40% by mass ammonia sulfate solution with pH at neutral.

EXAMPLE 10

The U.S. operates over one hundred and sixty commercial anaerobic digesters on CAFOs, producing 50 MW of power and mitigating over 1 million metric tons of $CO_2$ equivalents in greenhouse gas emissions. Although recent years have shown acceleration in adoption rates, traditionally-low received electrical sale receipts for the U.S. and concerns with existing manure infrastructure and manure handling operations (why less than 20% of systems exist on swine and feedlot operations) remain primarily responsible for keeping AD well below its stated potential.

Figure 14:
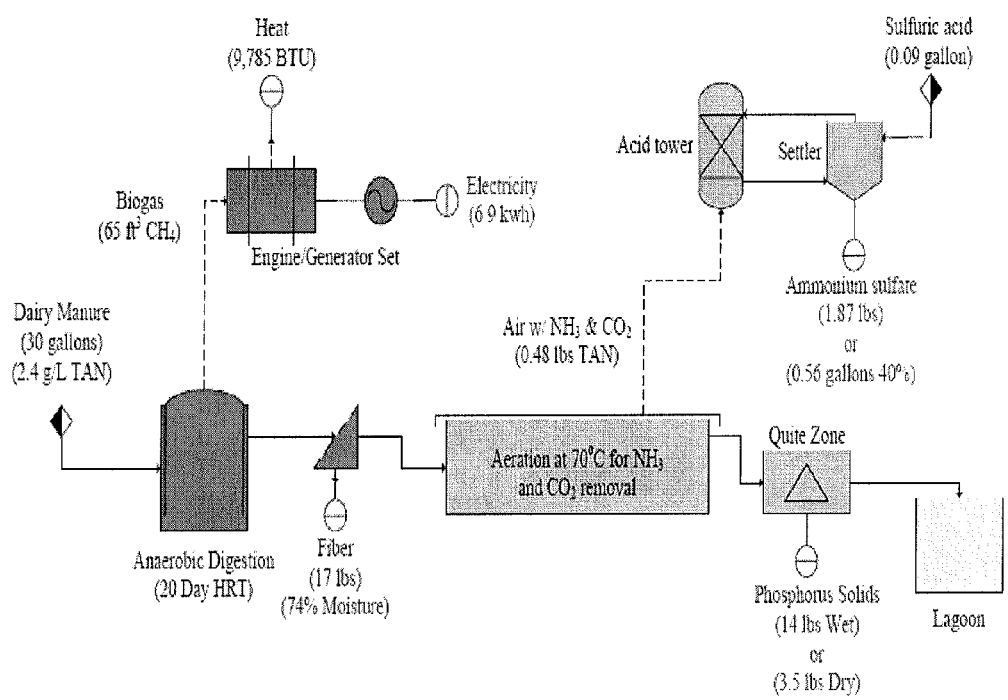
FIG. 14 is a schematic depicting mass flow from a dairy anaerobic digester and nutrient recovery system (/cow/day basis).

FIG. 14 is a schematic depicting a mass flow for a typical anaerobic digester and nutrient recovery system on a dairy, based on a cow/day basis. Mass flow inputs and outputs are based on data obtained during nutrient recovery pilot testing as well as data developed by Frear et al (2010) during long-term evaluation of a commercial dairy AD.

Products and revenue streams produced from a combination anaerobic digester/nutrient recovery system include electricity, fiber, ammonia sulfate slurry and P-rich solids. When cost inputs and revenue streams are calculated into the mass balance, an overall accounting of project economics and financing can be developed as described in Table 6.

TABLE 6

Input costs (Electrical, chemical, O&M, labor) and product revenues (/cow/day basis)

| | Inputs | | | Products | |
|---|---|---|---|---|---|
| Item | Quantity | $/cow/day | Item | Quantity | $/cow/day |
| AD Power (5¢/KWh) | 0.69 KWh | $0.035 | Power (8¢/KWh) | 6.9 KWh | $0.55 |
| NR Power (5¢/KWh) | 2.1 KWh | $0.11 | NR Power (8¢/KWh) | — | — |
| $H_2SO_4$ ($175/ton) | 1.4 lbs | $0.12 | Fiber ($10/wet ton) | 17 lbs | $0.085 |
| AD O&M (5% AC) | | $0.21 | P-Solids ($175/dry ton) | 3.5 lbs | $0.31 |
| NR O&M (2% AC) | | $0.03 | N-Salt ($338/k gallons) | 0.56 | $0.19 |
| NR Labor (0.5 FTE) | | $0.06 | Other (Tipping, credits) | — | — |
| Total AD only | | $0.25 | Total AD only | | $0.55 |
| Total NR only | | $0.32 | Total NR only | | $0.59 |
| Total AD + NR | | $0.57 | Total | | $1.14 |

Average received electrical power prices in Pacific Northwest (US-EIA, 2007); AD parasitic power demand is 10% (Andgar, 2010) while NR parasitic power demand is directly calculated from pilot tests.
Average received sulfuric acid price (ICIS Chemical Market Reporter, 2010)
AD O&M is 5% of AD capital cost ($1,500/cow) while NR O&M is at 2% of NR capital cost ($500/cow) (Andgar, 2010)
NR Labor is estimated to require ½ FTE semi-skilled personnel ($40,000/yr).
Fiber product viewed as bedding replacement to existing alternatives (Andgar, 2010)
Estimate of organic certified P-solids sale price assuming 4:2:1 dry weight fertilizer grade (Wolfkill Fertilizer and Feed, 2010)
Estimate of ammonia sulfate slurry (40% by mass) sale price (Wilson Industrial, 2010)

From Table 6, it can be seen that anaerobic digestion systems have relatively low revenue to operating cost ratio (~2:1) as well as low farm receipts, which are primarily dependent upon sales of low value electrical commodity, which explains some of the previously discussed concerns regarding digester economics and adoption. At a $1,500/cow capital cost structure and annualized revenue of roughly $200/cow per year, a capital cost payback period becomes 7-8 years, which is somewhat long for some financing partners. This is why most on-farm, dairy digesters are actively practicing co-digestion so that they can obtain extra revenue from received tipping fees as well as the extra electrical production from the higher energy waste stream producing more biogas.

Co-digestion at relatively low volumetric loadings can lead to important gains in revenues and project financing. In their particular case study, total project revenues nearly tripled with only a 20% substitution with off-farm substrates, significantly improving on annual profits and capital payback. As noted, co-digestion brings extra nutrients to the farm gate and therefore makes concerns on nutrient over-loading to fields even more of a problem, thus the need for a nutrient recovery mechanism to go along with the digestion system. Importantly, Table 6 also shows that when nutrient recovery is included as part of an entire AD/NR project, the revenue to operating cost ratio stays approximately the same, thereby not improving upon overall economics, but importantly not making the situation worse while improving upon an important farm and environmental concern.

EXAMPLE 11

The problem facing the U.S. caged layer industry and its 400+ larger CAFO-sized farms, representing 75% of total US inventory (USDA NASS, 2009), is how to annually treat 4 million tons of wet manure (Mukhtar, 2007) in a manner that responds to emerging needs in renewable energy, meeting new air/water quality standards, and establishing new revenue streams for enhanced farm sustainability. The status quo of field application of manure with or without compost treatment is quickly becoming out-dated technology in the 21$^{st}$ century, which is focused on waste treatment while also producing renewable energy. However, next generation technology options allowing for production of renewable energy, such as gasification and anaerobic digestion have technical concerns, as applied to caged layer manure.

Gasification, while suited well for dry broiler litter operations (80% total solids (TS)), is poorly positioned for much wetter caged layer manure (25% TS) while AD has historically not been identified as a suitable technology for poultry manure/litter because of its inability to handle the high solid content and biologically-inhibitory levels of ammonia (Abouelenien et al, 2010). The opportunity lies in demonstrating that existing commercial anaerobic digestion units can be effectively and economically operated using caged layer manure if the digester effluent is treated with a nutrient recovery system as described in the disclosure herein.

Caged poultry manure with 25% TS requires an input of dilution water in order to supply a wastewater material suitable for operation within commercially-available anaerobic digester technologies. On-farm, manure-based anaerobic digester units within the US have traditionally used complete-mix (various European or US designs) or mixed plug-flow (GHD Inc., Chilton, Wis.) technology, with both technologies ideally supporting influents with TS content on the order of 4-12% (US-EPA, 2006). However, mixed plug-flow, representing 70% of the US market share, offers a more reliable technology option for the higher range of solid flows. With caged-layer manure arriving from the belt press with TS of 25%, it is clear that effective performance of the digesters require more than a 1:1 dilution with water, and at the scale of 600,000 layers for an average operation, that amounts to more than 180,000 gallons of dilution water per day—a sum that is simply not sustainable or economical, particularly in water threatened regions of the US. The conclusion, then, is that, in order for effective anaerobic digestion of caged layer manure to occur, an alternative to fresh water for dilution is required and that source is the anaerobic digester effluent itself, which with treatment can be used as reclaim water.

Anaerobic digester effluent as a source of reclaim water is viable, but only upon treatment and preparation. Since typical anaerobic digester manure systems result on the order of 30-40% TS destruction, a system with influent of 11% TS leads to effluent with a 7% TS. Re-use of 7% TS effluent as dilution water makes poor engineering sense as every percentage point of solids that is re-introduced to the front of the digester results in the need for more reclaim water to attain the desired working TS flow rate. From a biological sense, the operation is non-optimal as well, as the non-digested solids are for the most part inert or recalcitrant in nature, which would lead to little further degradation upon extended digestion, thereby filling a fraction of the digester volume with non-reactive, non-biogas producing material.

Research and commercial demonstration have already shown that industrial separation of a significant portion of the solids can be accomplished using decanting centrifuges (Wenning Poultry, Fort Recovery, Ohio). While, utilization of these industrial separators requires additional capital and operating input, not to mention, parasitic use of produced electricity, it does serve to accomplish two very important goals. First, the effluent liquid to be used as reclaim water can be brought to a more desirable TS content on the order of 2% TS. Importantly, the remaining solids are suspended solids, which supply both nutrients and some biodegradable material to the digester, while minimizing the volumetric impact to the digester. Of equal importance is research that shows during the digestion process, a significant portion of the organic phosphorus is converted to inorganic form and when in the presence of high magnesium and calcium content manures, is chemically converted to phosphates bound as amorphous micro-solid salts. Thus, decanting centrifuge of the solids within the effluent serves as a recovery mechanism and concentrator for P in the form of saleable organic solids.

Figure 15:
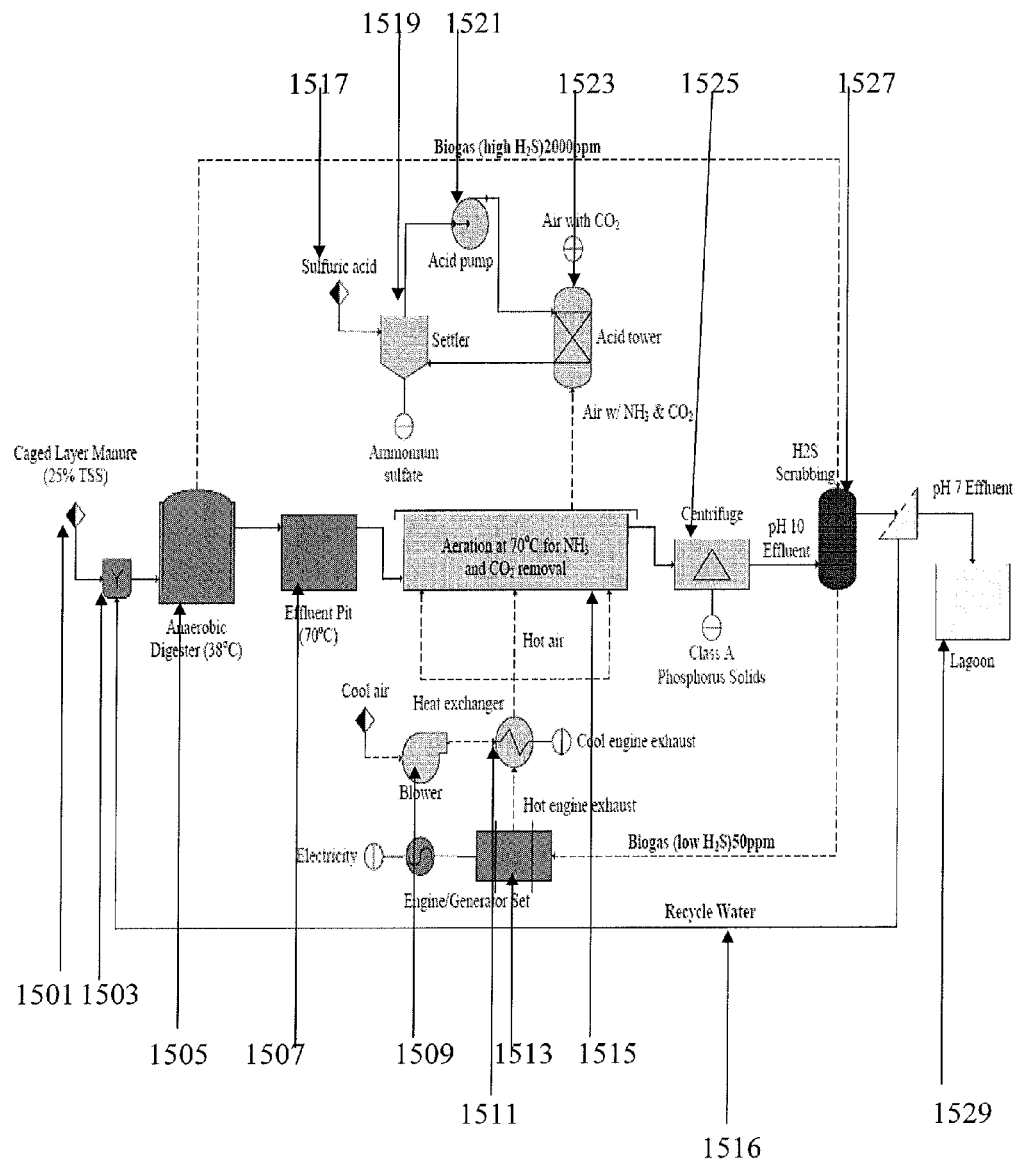
FIG. 15 is a schematic of anaerobic digester and nutrient recovery system in poultry manure digester.

As depicted in the schematic in FIG. 15, aeration at 70° C. (1515), which allows for supersaturated $CO_2$ to be released from the liquid to gas phase, is followed by centrifugation (1517). Centrifugation allows the total solids content in the effluent to be reduced. In addition, the solids that remain are high in nutrient content and are typically biodegradable.

Figure 16:
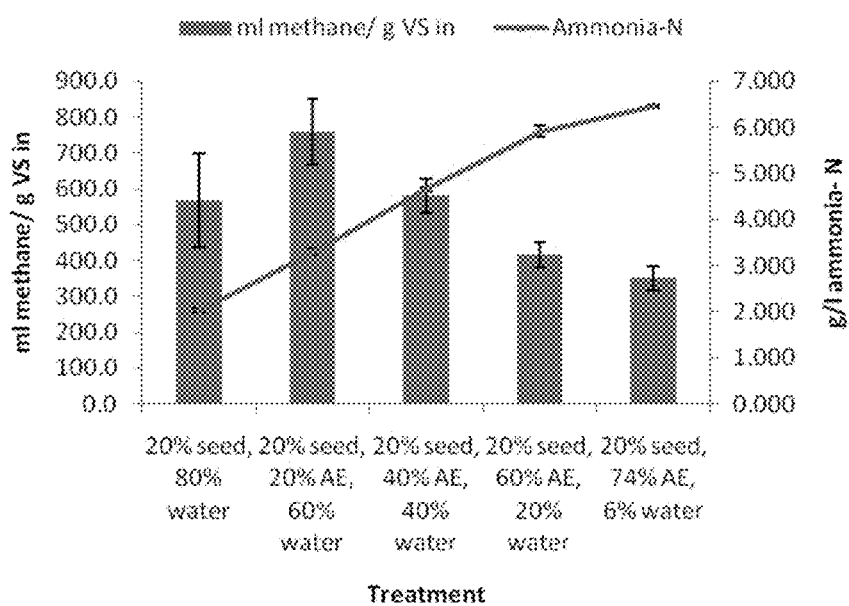
FIG. 16 is a bar graph demonstrating that methane production as factor of TAN concentration and use of anaerobic digester effluent as reclaim water (i.e. 20:20:60 AE:W refers to 20% seed and 20% anaerobic digester effluent mixed with 60% fresh water as source of reclaim water during digestion).

While removal of solids allows for improved utilization of AD effluent as reclaim water, it does not solve an important concern regarding retention of soluble ammonia and the inhibition that it contributes to the anaerobic digester process. Ammonia inhibition has been extensively studied during the anaerobic digestion of poultry manure, with results showing that poultry manure has levels of total ammonia nitrogen (TAN), at times, well above levels of threshold inhibition identified as at or above 2 g/L TAN (Koster and Letting a, 1984). Research at Washington State University (WSU) has shown that: (1) layer manure TAN levels are significantly higher than the threshold; (2) levels become increasingly and dangerously high as AD effluent is used as reclaim water, and (3) biogas performance steadily declines with increased ammonia and use of reclaim water, especially when TAN levels exceed 4 g/L (FIG. 16).

Thus, in order to effectively utilize AD effluent for reclaim water, it will be important to first remove the soluble ammonia. One industry standard method for removal of soluble ammonia from wastewaters is ammonia stripping followed by chemical stabilization of the recovered ammonia as ammonia salts, i.e. ammonia sulfate through the use of an acid contact chamber. The methods and systems disclosed herein can achieve this goal.

EXAMPLE 12

Figure 17:
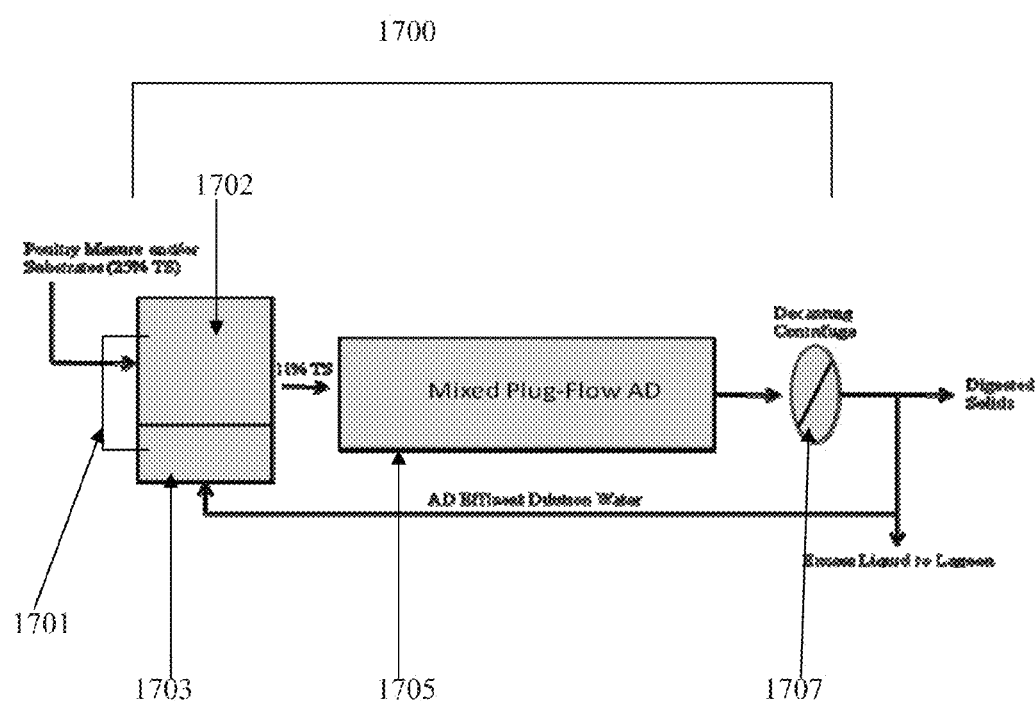
FIG. 17 is a schematic of a commercial anaerobic digester for a caged layer operation.

An example of a commercial system (1700) of anaerobic digestion on caged layer operation is shown in FIG. 17. A two chamber reception pit (1701) first receives the feedstocks to the digester. The larger of the two chambers (1702) is the mixing pit for the poultry manure, any outside co-digestion substrates, and the recycle water that is used as needed. All of the liquid effluent from the post-digestion decanting centrifuge (1707) goes from the centrifuge, through the smaller of the two chambers (1703) of the reception pit (1701) and this chamber overflows to a small liquid storage lagoon. This design ensures that the small chamber (1703) is always full and has sufficient volume of stored, digested and centrifuged liquid to blend with the poultry manure as needed in volume for TS reduction prior to pumping from the larger chamber (1702) into the digester (1705).

The present mixing tank and decanting centrifuge design has allowed for a consistent supply of 10-12% TS manure wastewater to the digester and thereby allowed for a suitable influent for operation within the mixed plug-flow digester. This system solves the concern for non-fresh dilution water and the need to spin-off contained suspended solids within the dilution.

EXAMPLE 13

Figure 18:
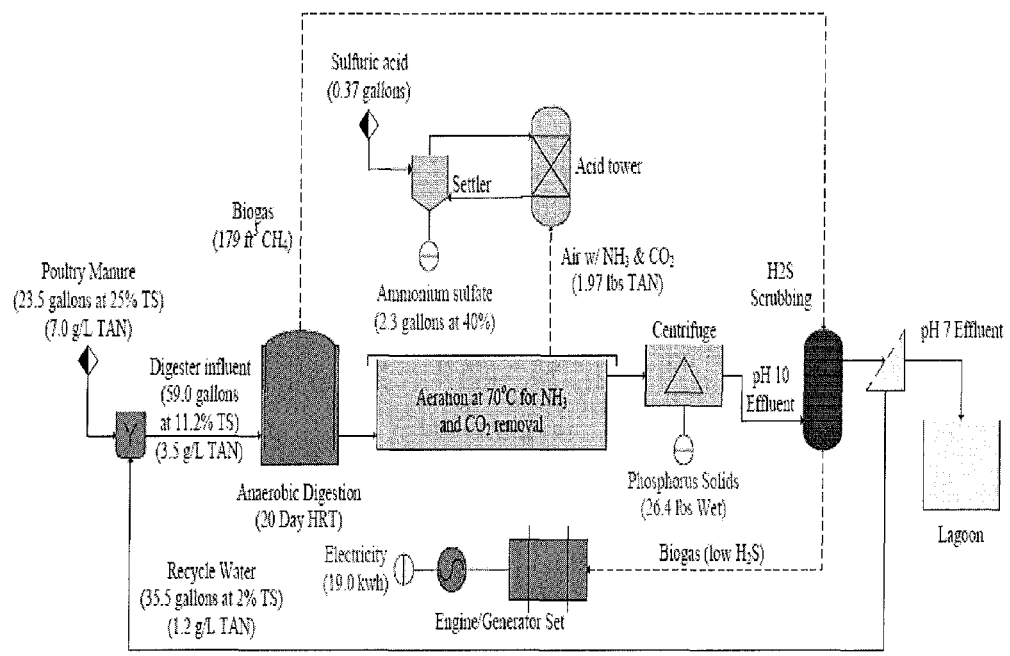
FIG. 18 is a schematic of a mass flow layer anaerobic digester and nutrient recovery system (1,000 layer/day basis).

FIG. 18 is a schematic depicting mass balance and flow for a caged layer poultry facility based on a 1,000 per day basis. The mass balance can assist in generating a table comparing input costs (electrical, chemical, O&M, labor) with revenue projections, thereby developing a concept of potential project income and capital expenditure pay back periods (Table 7).

TABLE 7

| Input costs and product revenues (/1,000 layers/day basis) | | | | | |
|---|---|---|---|---|---|
| Inputs | | | Products | | |
| Item | Quantity | $/1000/day | Item | Quantity | $/1000/day |
| AD Power (5¢/KWh) | 1.90 KWh | $0.095 | AD Power (8¢/KWh) | 19.0 KWh | $1.52 |
| NR Power (5¢/KWh) | 2.64 KWh | $0.13 | NR Power (8¢/KWh) | — | — |
| $H_2SO_4$ ($175/ton) | 5.7 lbs | $0.50 | Fiber ($10/wet ton) | — | — |
| AD O&M (5% AC) | | $0.90 | P-Solids ($300/dry ton) | 5.3 lbs | $0.80 |
| NR O&M (2% AC) | | $0.06 | N-Salt ($634/k gallons) | 2.3 gal | $1.46 |
| NR Labor (0.5 FTE) | | $0.06 | Other (Tipping, credits) | — | — |

TABLE 7-continued

Input costs and product revenues (/1,000 layers/day basis)

| | Inputs | | Products | | |
|---|---|---|---|---|---|
| Item | Quantity | $/1000/day | Item | Quantity | $/1000/day |
| Total AD only | | $1.00 | Total AD only | | $1.52 |
| Total NR only | | $0.75 | Total NR only | | $2.26 |
| Total AD + NR | | $1.75 | Total | | $3.78 |

Average received electrical power prices in Pacific Northwest (US-EIA, 2007); AD parasitic power demand is 10% (Andgar, 2010) while NR parasitic power demand is directly calculated from pilot tests.
Average received sulfuric acid price (ICIS Chemical Market Reporter, 2010)
AD O&M is 5% of AD capital cost ($6,600/1000 layers) while NR O&M is 2% of capital cost ($1,000/1000 layers) (GHD, 2010)
NR Labor is estimated to require ½ FTE semi-skilled personnel ($40,000/yr).
Estimate of organic certified P-solids sale price assuming 4:2:1 dry weight fertilizer grade (Wolfkill Fertilizer and Feed, 2010)
Estimate of ammonia sulfate slurry (40% by mass) sale price (Wilson Industrial, 2010)

As with dairy AD, the revenue to input ratio is rather small, but in this case below 2:1 and more near 1.5:1. With a capital expenditure of AD alone of $6,600/1,000 layer, yearly revenues lead to an estimated payback period of 12 years, clearly a long and non-preferred project length. As a result AD alone of layer manure would require co-digestion and/or other financing mechanisms (tax credits, carbon credits, etc.) to be economically feasible, and has already been shown, co-digestion or even non-co-digestion are not viable options as either way the ammonia and N loading would both inhibitory and problematic to the digester and farm, respectively. However, when nutrient recovery is attached to anaerobic digestion, the revenue to input ratio rises to 2.2:1, significantly increasing revenues and lowering the estimated payback period to 5-6 years. Thus, not only does nutrient recovery of layer manure allow for anaerobic digestion to be technically feasible, it also significantly improves upon the project economics.

EXAMPLE 14

The methods and systems disclosed herein have the unique ability to serve two different applications: (1) low-cost P recovery only and (2) higher cost nitrogen and phosphorous recovery; opening up the technology to a wide assortment of farm sizes and farm nutrient applications. Aeration allows for the settling of phosphorous-solids, however low temperature, shorter length and/or lower aeration rate can induce a pH change that stimulates settling of phosphorous-solids without an associated release of ammonia. In such a case, there is no need to harvest the ammonia and utilize sulfuric acid to sequester it as a salt. By removing this need a farm that is not under N nutrient management and that is too small to take on the added capital and operating costs of a full system can still accomplish phosphorous-removal—at low capital and operating cost. Table 8 below summarizes data collected from pilot scale work using the reduced input system.

TABLE 8

Phosphorous-recovery only

| | TS (%) | VS (%) | TN (g/L) | TAN (g/L) | TP (mg/L) |
|---|---|---|---|---|---|
| Effluent Pit Only Aeration Experiment | | | | | |
| Big Sky Manure Effluent w/Fiber | 5.15 | 3.28 | 4.03 | 2.61 | 564.53 |
| Six hours of aeration at 35 C. and 40 gal/cfm | 4.32 | 2.65 | 4.23 | 2.58 | 613.48 |

TABLE 8-continued

Phosphorous-recovery only

| | TS (%) | VS (%) | TN (g/L) | TAN (g/L) | TP (mg/L) |
|---|---|---|---|---|---|
| Post fiber separation (18 mesh) | 4.33 | 2.45 | 3.78 | 2.63 | 593.90 |
| 1 day settling | 2.51 | 1.38 | 3.18 | 2.46 | 231.69 |
| 2 days settling | 2.43 | 1.32 | 3.18 | 2.42 | 199.06 |
| 3 days settling | 2.41 | 1.29 | 3.18 | 2.38 | 199.06 |
| Beginning to End Reduction (%) | 53.20 | 60.67 | 21.09 | 8.81 | 64.74 |
| Effluent Pit + Extra Aeration Experiment | | | | | |
| Big Sky Manure Effluent w/Fiber | 5.15 | 3.28 | 4.03 | 2.61 | 564.53 |
| Six hours of aeration at 40 gal/cfm | 5.37 | 3.41 | 4.09 | 2.65 | 587.38 |
| Post fiber separation (18 mesh) | 4.47 | 2.49 | 3.87 | 2.64 | 600.43 |
| Add 18 hrs aeration at 20 C. and 40 gal/cfm | 4.37 | 2.48 | 3.71 | 2.48 | 580.85 |
| 1 day settling | 2.27 | 1.21 | 3.01 | 2.23 | 133.79 |
| 2 days settling | 2.24 | 1.17 | 2.94 | 2.23 | 124.00 |
| 3 days settling | 2.19 | 1.14 | 2.92 | 2.22 | 114.21 |
| Beginning to End Reduction (%) | 57.48 | 65.24 | 27.54 | 14.94 | 79.77 |

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations that operate according to the principles of the invention as described. Therefore, it is intended that this invention be limited only by the claims and the equivalents thereof. The disclosures of patents, references and publications cited in the application are incorporated by reference herein in their entirety.

We claim:

1. A method for recovering a nutrient comprising:
   (a) heating and aerating anaerobic digester effluent in an aeration reactor for a time period ranging from 12 hours to 36 hours to convert soluble ammonium to gaseous ammonia;
   (b) providing gaseous ammonia from the aeration reactor to a stripping tower, said stripping tower providing controlled amounts of acid that reacts with gaseous ammonia; and
   (c) recovering an ammonium salt produced from reacting the acid with gaseous ammonia in the stripping tower.

2. The method of claim 1, wherein heating the anaerobic digester effluent comprises using a heat exchanger with the exhaust from a biogas engine generator as the heated air stream.

3. The method of claim 1, wherein heating the anaerobic digester effluent comprises heating the effluent to a temperature from about 140° F. to about 170° F.

4. The method of claim 1, wherein aerating the anaerobic digester effluent is accomplished using micro-aerators that aerate the effluent at a rate from 5 gallons/cfm to 25 gallons/cfm.

5. The method of claim 1 further comprising pumping the anaerobic digester effluent from the aeration reactor to a solids settling system after providing the gaseous ammonia to the stripping tower.

6. The method of claim 5 further comprising collecting phosphorous-rich solids from the solids settling system.

7. The method of claim 5, further comprising digesting waste fibrous material in an anaerobic digester prior to step (a).

8. The method of claim 7 further comprising pumping the effluent from the solids settling system to a vessel and reacting biogas from the digester with the effluent to return the effluent pH to neutral and reduce the amount of hydrogen sulfide in the biogas.

9. The method of claim 1, wherein the stripping tower comprises a two tower system, wherein each tower of the two tower system provides controlled amounts of acid that reacts with gaseous ammonia.

10. A method for recovering a nutrient comprising:
(a) heating anaerobic digester effluent containing fibrous solids and suspended solids to about 160° F.;
(b) separating fibrous solids from the suspended solids in the effluent;
(c) heating and aerating the effluent in an aeration reactor for a time period ranging from 12 hours to 36 hours to convert soluble ammonium to gaseous ammonia;
(d) providing gaseous ammonia from the aeration reactor to a stripping tower, said stripping tower providing controlled amounts of acid to react with gaseous ammonia; and
(e) recovering an ammonium salt produced from reacting the acid with gaseous ammonia in the stripping tower.

11. The method of claim 10, wherein the stripping tower comprises a two tower system, wherein each tower of the two tower system provides controlled amounts of acid that reacts with gaseous ammonia.

12. A method for recovering a nutrient comprising:
(a) heating and aerating anaerobic digester effluent in an aeration reactor to convert soluble ammonium to gaseous ammonia;
(b) providing gaseous ammonia from the aeration reactor to a first stripping tower, said stripping tower providing controlled amounts of acid that reacts with gaseous ammonia;
(c) providing unreacted gaseous ammonia from the first stripping tower to a second stripping tower, said second stripping tower providing controlled amounts of acid that reacts with gaseous ammonia; and
(d) recovering an ammonium salt produced from reacting the acid with gaseous ammonia in the first and second stripping tower.

* * * * *